US005604131A

United States Patent [19]
Wadsworth et al.

[11] Patent Number: 5,604,131
[45] Date of Patent: Feb. 18, 1997

[54] CDNA-GENOMIC DNA HYBRID SEQUENCE ENCODING APP770 CONTAINING A GENOMIC DNA INSERT OF THE KI AND OX-2 REGIONS

[75] Inventors: Samuel Wadsworth, Shrewsbury; Benjamin Snyder, Worcester; Vermuri B. Reddy; Chamer Wei, both of Westborough, all of Mass.

[73] Assignee: Athena Neurosciences, Inc., South San Francisco, Calif.

[21] Appl. No.: 123,702

[22] Filed: Sep. 17, 1993

Related U.S. Application Data

[63] Continuation of Ser. No. 817,584, Jan. 7, 1992, abandoned.
[51] Int. Cl.[6] ........................... C07H 21/04; C12N 15/12; C12N 15/63
[52] U.S. Cl. .................... 435/320.1; 536/23.5; 536/24.1; 935/10
[58] Field of Search ........................... 800/2; 435/172.3; 424/9

[56] References Cited

U.S. PATENT DOCUMENTS 5,387,742  2/1995  Cordell .

FOREIGN PATENT DOCUMENTS

| 0451700AT | 4/1991 | European Pat. Off. . |
| WO89/06689 | 7/1989 | WIPO . |
| WO91/19810 | 12/1991 | WIPO . |
| WOA9206187 | 4/1992 | WIPO . |
| WOA9213069 | 8/1992 | WIPO . |
| WOA19302189 | 2/1993 | WIPO . |

OTHER PUBLICATIONS

Games et al. (1995) Nature 373, 523–527.
Genetic Eng. News, Mar. 1, 1995, pp. 1,3 & 31.
Duff et al. (1993) Nature 373, 476–477.
Price et al (1993) Proced. Natl. Acad. Sci 90, 6381–6384.
Burke et al (1987) Science 236, 806–812.
Mansour et al (1988) Nature 336, 348–353.
Salbaum et al (1988) EMBO J. 7, 2807–2813.
Scangos, et al., "Gene Transfer into Mice" Adv. in Genet. 24, 285–322 (1987).
Sakimura et al (1987) Gene 60, 103–113.
Swanson et al (1985) Nature 317, 363–366.
N. Argyle, et al., "Psychogeriatric Patients: Their Supporters' Problems", Age and Ageing 14: 355–360 (1985).
B. Brown, et al., "Axonal Polypeptides Cross–Reactive with Antibodies to Neurofilament Proteins," Journal of Neurochemistry 40(2): 299–308 (1983).
M. Chartier–Harlin, et al., "Early–Onset Alzheimer's Disease Caused by Mutations at Codon 717 of the β–Amyloid Precursor Protein Gene," Nature 353: 844–846 (Oct. 31, 1991).
W. Chou, et al. "Alzheimer Cortical Neurons Containing Abundant Amyloid mRNA, Relationship to Amyloid Deposition and Senile Plaques," Journal of Psychiatric Research 24(1): 37–50 (1990).

F. David, et al., "Absence of a Close Linkage Between Alzheimer's Disease Susceptibility Gene and a Polymorphic DNA Probe Coding for β–Amyloid," Biomedicine & Pharmacotherapy 42: 575–578 (1988).
P. Davies, "Alz–50, A68, and the Paired Helical Filaments of Alzheimer's Disease," The Journal of NIH Research 3: 53–56 (Nov. 1991).
F. DeFeudis, "Beta–Amyloid Protein in Transgenic Mice," Drug News & Perspectives 4(10): 617–619 (Dec. 1991).
J. Delabar, et al., "β Amyloid Gene Duplication in Alzheimer's Disease and Karyotypically Normal Down Syndrome," Science 235: 1390–1392 (Mar. 13, 1987).
J. Flood, et al., "Amnestic Effects in Mice of Four Synthetic Peptides Homologous to Amyloid β Protein from Patients with Alzheimer Disease," Proceedings of the National Academy of Science (U.S.A.) 88: 3363–3366 (Apr. 1991).
H. Furuya, et al., "Amyloid β–Protein Gene Duplication is not Common in Alzheimer's Disease: Analysis by Polymorphic Restriction Fragments," Biochemical and Biophysical Research Communications 150(1): 75–81 (Jan. 15, 1988).
J. Garfield, et al., "Differential Effects of Ketamine Stereoisomers on Maze Performance in the Mouse," Anesthesiology 63: 681–683 (1985).
N. Glanville, et al., "Structure of Mouse Metallothionein–I Gene and its mRNA," Nature 292: 267–269 (Jul. 16, 1981).
G. Glenner, et al., "Alzheimer's Disease: Initial Report of the Purification and Characterization of a Novel Cerebrovascular Amyloid Protein," Biochemical and Biophysical Research Communications 120(3): 885–890 (May 16, 1984).
A. Goate, et al., "Segregation of a Missense Mutation in the Amyloid Precursor Protein Gene with Familial Alzheimer's Disease," Nature 349: 704–706 (Feb. 21, 1991).
T. Golde, et al., "Expression of β Amyloid Protein Precursor MRNAs: Recognition of a Novel Alternatively Spliced Form and Quantitation in Alzheimer's Disease Using PCR," Neuron 4: 253–267 (Feb. 1990).
D. Goldbaber, et al., "Characterization and Chromosomal Localization of a cDNA Encoding Brain Amyloid of Alzheimer's Disease," Science 235: 877–880 (Feb. 20, 1987).
R. Hammer, et al., "Spontaneous Inflammatory Disease in Transgenic Rats Expressing HLA–B27 and Human β$_2$m: An Animal Model of HLA–B27–Associated Human Disorders," Cell 63: 1099–1112 (Nov. 30, 1990).
E. Jenkins, et al., "Fine Mapping of an Alzheimer Disease–Associated Gene Encoding Beta–Amyloid Protein," Biochemical and Biophysical Research Communications 151(1): 1–8 (Feb. 29, 1988).

(List continued on next page.)

Primary Examiner—Jacqueline M. Stone
Assistant Examiner—Deborah Crouch
Attorney, Agent, or Firm—Arnall Golden & Gregory

[57] ABSTRACT

A nucleic acid construct is described which when expressed in cells, results in the production of APP695, APP751 and APP770. The construct is the cDNA for APP770 with the genomic sequences encoding the KI and OX-2 regions substituting for those regions present in the cDNA.

3 Claims, 26 Drawing Sheets

OTHER PUBLICATIONS

C. Joachim, et al., "Amyloid β–Protein Deposition in Tissues Other than Brain in Alzheimer's Disease," *Nature* 341: 226–230 (Sep. 21, 1989).

J. Kang, et al., "The Precursor of Alzheimer's Disease Amyloid A4 Protein Resembles a Cell–Surface Receptor," *Nature* 325: 733–736 (Feb 19, 1987).

R. Katzman, "Alzheimer's Disease," The New England Journal of Medicine 314(15): 964–973 (Apr. 10, 1986).

S. Kawabata, et al., "Amyloid Plaques, Neurofibrillary Tangles and Neuronal Loss in Brains of Transgenic Mice Overexpressing a C–Terminal Fragment of Human Amyloid Precursor Protein," *Nature* 354: 476–478 (Dec. 12, 1991).

M. Kidd, "Paired Helical Filaments in Electron Microscopy of Alzheimer's Disease," *Nature* 197: 192–193 (Jan. 12, 1963).

N. Kitaguchi, et al., "Novel Precursor of Alzheimer's Disease Amyloid Protein Shows Protease Inhibitory Activity," *Nature* 331: 530–532 (Feb. 11, 1988).

N. Kowall, et al., "An In Vivo Model for the Neurodegenerative Effects of β Amyloid and Protection by Substance P," *Proceedings of the National Academy of Science (U.S.A.)* 88: 7247–7251 (Aug. 1991).

V. Lee, "Unraveling the Mystery of the Paired Helical Filaments of Alzheimer's Disease," *The Journal of NIH Research* 3: 52–55 (Nov. 1991).

H. Lemaire, et al., "The PreA4$_{695}$ Precursor Protein of Alzheimer's Disease A4 Amyloid is Encoded by 16 Exons," *Nucleic Acids Research* 17(2): 517–522 (1989).

E. Levy, et al., "Mutation of the Alzheimer's Disease Amyloid Gene in Hereditary Cerebral Hemorrhage, Dutch Type," *Science* 248: 1124–1126 (Jun. 1990).

R, Majocha, et al., "Immunostaining of Neurofilament Protein in Human Postmortem Cortex: A Sensitive and Specific Approach to the Pattern Analysis of Human Cortical Cytoarchitecture," *Canadian Journal of Biochemistry and Cell Biology* 63: 577–584 (1985).

R. Majocha, et al. "Monoclonal Antibody to Embryonic CNS Antigen A2B5 Provides Evidence for the Involvement of Membrane Components at Sites of Alzheimer Degeneration and Detects Sulfatides as Well as Gangliosides," *Journal of Neurochemistry* 53(3): 953–961 (1989).

R. Manning, et al., "Identification in Rodents and other Species of an mRNA Homologous to the Human β–Amyloid Precursor," *Molecular Brain Research* 3: 293–298 (1988).

C. Marotta, et al., "Overexpression of Amyloid Precursor Protein A4 (β–Amyloid) Immunoreactivity in Genetically Transformed Cells: Implications for a Cellular Model of Alzheimer Amyloidosis," *Proceedings of the National Academy of Science (U.S.A.)* 86: 337–341 (Jan. 1989).

L. Martin, et al., "Amyloid Precursor Protein in Aged Nonhuman Primates," *Proceedings of the National Academy of Science (U.S.A.)* 88: 1461–1465 (Feb. 1991).

K. Maruyama, et al., "Formation of Amyloid–Like Fibrils in COS Cells Overexpressing Part of the Alzheimer Amyloid Protein Precursor," *Nature* 347: 566–569 (Oct. 11, 1990).

J. Marx, "Alzheimer's Research Moves to Mice," *Science* 253: 266–267 (Jul. 19, 1991).

J. Marx, "Mutation Identified as a Possible Cause of Alzheimer's Disease," *Science* 251: 876–877 (Feb. 22, 1991).

C. Masters, et al., "Amyloid Plaque Core Protein in Alzheimer's Disease and Down Syndrome," *Proceedings of the National Academy of Science (U.S.A.)* 82: 4245–4249 (Jun. 1985).

K. Mullis, et al., "Specific Synthesis of DNA in Vitro via a Polymerase–Catalyzed Chain Reaction," *Methods in Enzymology* 155: 335–350 (Academic Press, New York 1987).

J. Murrell, et al., "A Mutation in the Amyloid Precursor Protein Associated with Hereditary Alzheimer's Disease," *Science* 254: 97–99 (Oct. 4, 1991).

D. Patterson, et al., "Mapping of the Gene Encoding the β–Amyloid Precursor Protein and its Relationship to the Down Syndrome Region of Chromosome 21," *Proceedings of the National Academy of Science U.S.A.)* 85: 8266–8270 (Nov. 1988).

M. Pericak–Vance, et al., "Genetic Linkage Studies in Alzheimer's Disease Families," *Experimental Neurology* 102: 271–279 (1988).

M. Podlisny, et al., "Gene Dosage of the Amyloid β Precursor Protein in Alzheimer's Disease," *Science* 238: 669–671 9oct. 30, 1987).

P. Ponte, et al., "A New A4 Amyloid mRNA Contains a Domain Homologous to Serine Proteinase Inhibitors," *Nature* 331: 525–527 (Feb. 11, 1988).

D. Price, et al., "Alzheimer's Disease and Down's Syndrome," *Annals of New York Academy of Sciences*: 145–164 (1982).

D. Quon, et al., "Formation of β–Amyloid Protein Deposits in Brains of Transgenic Mice," *Nature* 352: 219–241 (Jul. 18, 1991).

V. Reddy, et al., "The Genome of Simian Virus 40," *Science* 200: 494–502 (May 5, 1978).

N. Robakis, et al., *"Molecular Cloning and Characterization of a CDNA Encoding the Cerebrovascular and the Neuritic Plaque Amyloid Peptides,"* Proceedings of the Natural Academy of Science (U.S.A.) 84: 4190–4194 (Jun. 1987).

P. St. George–Hyslop, et al., "Absence of Duplication of Chromosome 21 Genes in Familial and Sporadic Alzheimer's Disease," *Science* 238: 664–666 (Oct. 30, 1987).

P. St. George–Hyslop, et al., "The Genetic Defect Causing Familial Alzheimer's Disease Maps on Chromosome 21," *Science* 235: 885–890 (Feb. 20, 1987).

T. Saitoh, et al., "Secreted Form of Amyloid β Protein Precursor is Involved in the Growth Regulation of Fibroblasts," *Cell* 58: 615–622 (Aug. 25, 1989).

K. Sakimura, et al., "Partial Purification and Characterization of Messenger RNA Coding 14–3–2 Protein from Rat Brain," *Journal of Neurochemistry* 39(2): 336–370 (1982).

F. Sandhu, et al., "Expression of the Human β–Amyloid Protein of Alzheimer's Disease Specifically in the Brains of Transgenic Mice," *The Journal of Biological Chemistry* 266(32): 21331–21334 (Nov. 15, 1991).

D. Selkoe, "Amyloid Protein and Alzheimer's Disease," *Scientific American* 265(5): 68–76 (Nov. 1991).

D. Selkoe, "In the Beginning . . . " *Nature* 354: 432–433 (Dec. 12, 1991).

P. Southern, et al., "Transformation of Mammalian Cells to Antibiotic Resistance with a Bacterial Gene Under Control of the SV40 Early Region Promoter," *Journal of Molecular and Applied Genetics* 1(4): 327–341 (1982).

D. Spencer, et al., "Behavioral Impairments Related to Cognitive Dysfunction in the Autoimmune New Zealand Black Mouse," *Behavioral Neuroscience* 100(3): 353–358 (1986).

R. Tanzi, et al., "Amyloid β Protein Gene: cDNA, mRNA Distribution and Genetic Linkage Near the Alzheimer Locus," *Science* 235: 881–884 (Feb. 20, 1987).

R. Tanzi, et al., "The Amyloid β Protein Gene is not Duplucated in the Brains from Patients with Alzheimer's Disease," *Science* 238: 666–669 (Oct. 30, 1987).

R. Tanzi, et al., "The Genetic Defect in Familial Alzheimer's Disease is not Tightly Linked to the Amyloid β–Protein Gene," *Nature* 329: 156–157 (Sep. 10, 1987).

R. Tanzi, et al., "Molecular Genetic Approaches to Alzheimer's Disease," *Trends in Neuroscience* 12(4): 152–158 (1989).

R. Tanzi, et al., "Protease Inhibitor Domain Encoded by an Amyloid Protein Precursor mRNA Associated with Alzheimer's Disease," *Nature* 331: 523–530 (Feb. 11, 1988).

B. Tate-Ostroff, et al., "Identification of Cellular and Extracellular Sites of Amyloid Precursor Protein Extracytoplasmic Domain in Normal and Alzheimer Disease Brains," *Proceedings of the National Academy of Science (U.S.A.)* 86: 745–749 (Jan. 1989).

C. Van Broekhoven, et al., "Amyloid β Protein Gene and Hereditary Cerebral Hemorrhage with Amyloidosis (Dutch), "*Science* 248: 1120–1122 (Jun. 1990).

A. Weidemann, et al., "Identification, Biogenesis, and Localization of Precursors of Alzheimer's Disease A4 Amyloid Protein," *Cell* 57: 115–126 (Apr. 7, 1989).

D. Wirak, et al., "Deposits of Amyloid β Protein in the Central Nervous System of Transgenic Mice," *Science* 253: 323–325 (Jul. 19, 1991).

D. Wirak, et al., "Regulatory Region of Human Amyloid Precursor Protein (APP) Gene Promotes Neuron–Specific Gene Expression in the CNS of Transgenic Mice," *European Molecular Biology Organizaiton Journal* 10(2): 289–296 (1991).

M. Yamamoto, et al., "Effects of Indeloxazine Hydrochloride on Cognitive Disturbance in Cycloheximide–Treated Mice," *Journal of Pharmacy and Pharmacology* 41: 284–286 (1989).

Yoshikai, et al., "Genomic Organization of the Human Amyloid Beta–Protein Precursor Gene," *Gene:* 257–263 (1990).

Hyman, et al., "Amyloid, dementia and Alzheimer's disease" *Current Opinion in Neurology and Neurosurgery*, 1992, 5:88–93.

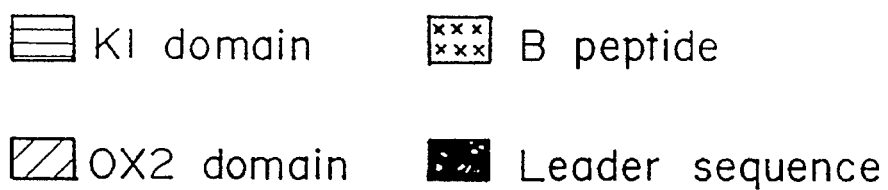
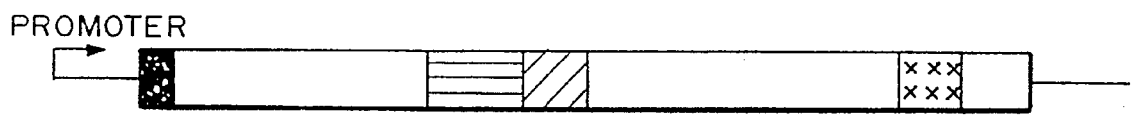
FIG. 1a
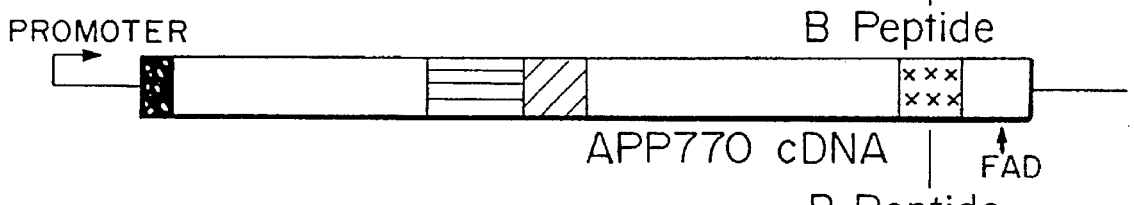
FIG. 1b
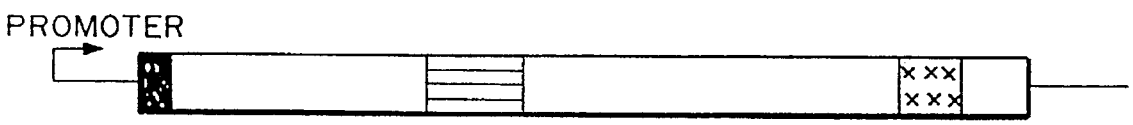
FIG. 2a
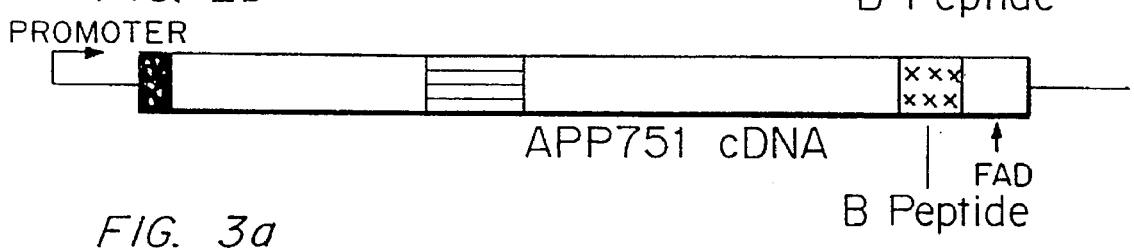
FIG. 2b
FIG. 3a
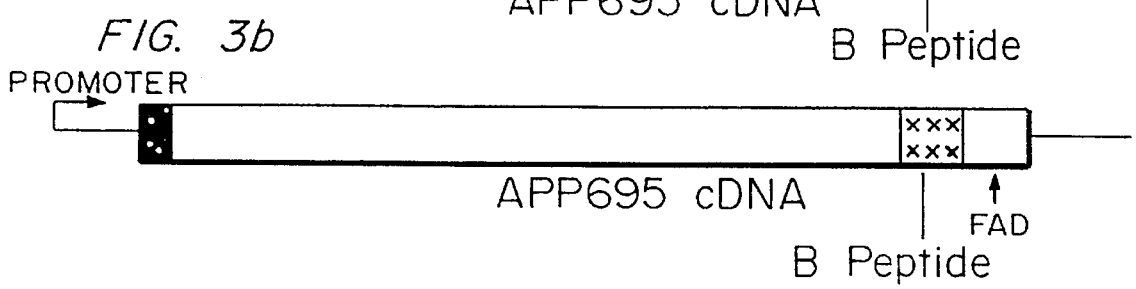
FIG. 3b

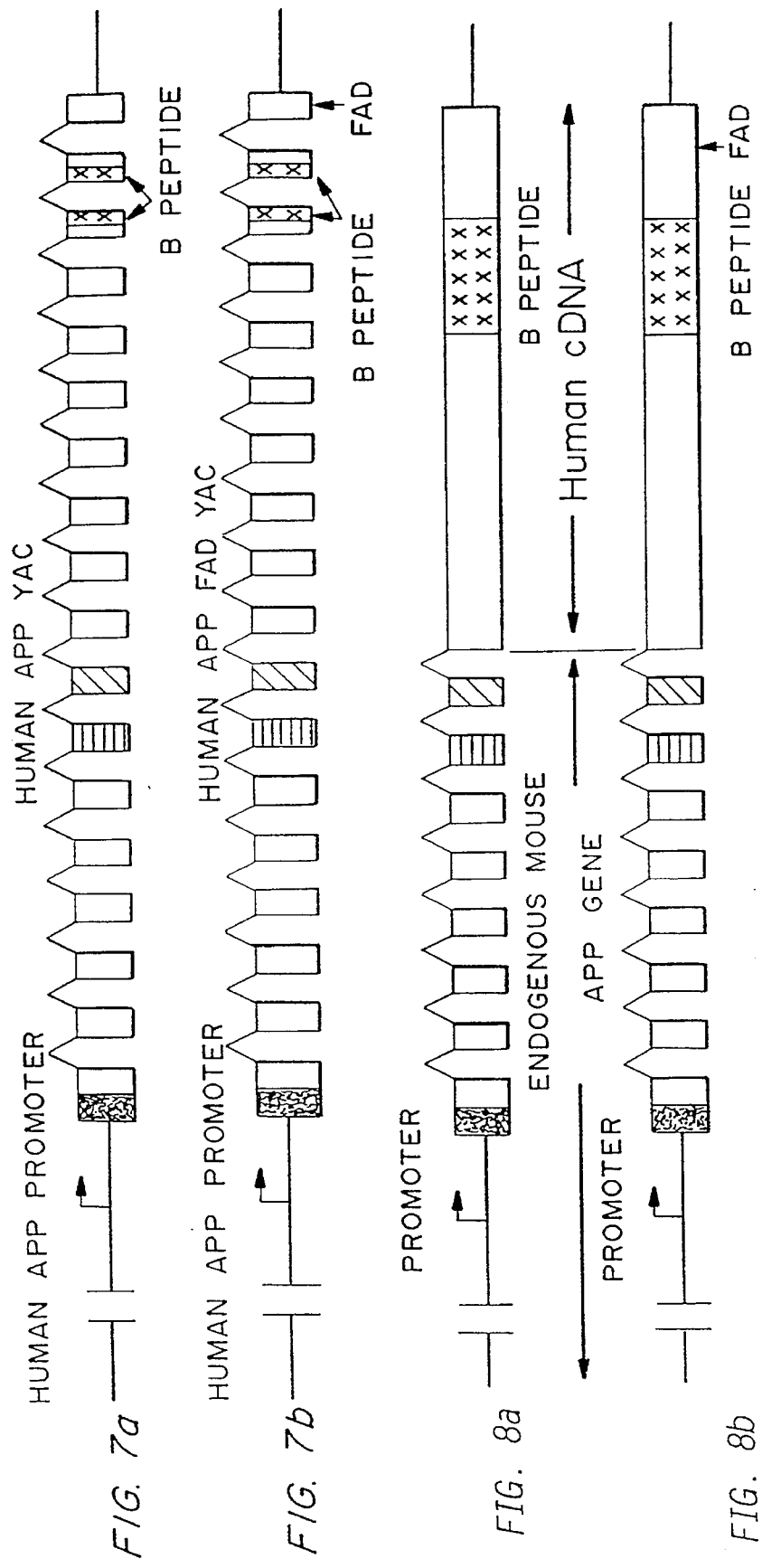

Figure 9A

```
                                              AGTTTCCTGGGCAGGGGTAGGCGAGA    -121
GCACGCGGGAGGAGCGTGCGCGGGCCCCGGGAGCAGCGGTGCGGGGTGGCGGGCGGGCAGAG              -61
CAAGGACGCGGGATCCCACTCGCGACAGCAGCGCCGTGCCCCGCCAGGGTCGCG                      -1
ATGCTGCCCGGTTTGGCACTGCTCCTGCTGGCCGCCTGGACGGCTCGGGCGCTGGAGGTA                 60
 M  L  P  G  L  A  L  L  L  L  A  A  W  T  A  R  A  L  E  V
 1                                 10                      20
CCCACTGATGGTAATGCTGGCCTGCTGGCTGAACCCCAGATTGCCATGTTCTGTGGCAGA                120
 P  T  D  G  N  A  G  L  L  A  E  P  Q  I  A  M  F  C  G  R
                     30                      40
CTGAACATGCACATGAATGTCCAGAATGGGAAGTGGGATTCAGATCCATCAGGACCAAA                 180
 L  N  M  H  M  N  V  Q  N  G  K  W  D  S  D  P  S  G  T  K
                     50                      60
ACCTGCATTGATACCAAGGAAGGCATCCTGCAGTATTGCCAAGAAGTCTACCCTGAACTG                240
 T  C  I  D  T  K  E  G  I  L  Q  Y  C  Q  E  V  Y  P  E  L
                     70                      80
CAGATCACCAATGTGGTAGAAGCCAACCAGCCAGTGACCATCCAGAACTGGTGCAAGCGG                300
 Q  I  T  N  V  V  E  A  N  Q  P  V  T  I  Q  N  W  C  K  R
                     90                     100
```

Figure 9B

```
GGCCGCAAGCAGTGCAAGACCCATCCCCACTTTGTGATTCCCTACCGCTGCTTAGTTGGT    360
 G  R  K  Q  C  K  T  H  P  H  F  V  I  P  Y  R  C  L  V  G
                                110                          120

GAGTTTGTAAGTGATGCCCTTCTCGTTCCTGACAAGTGCAAATTCTTACACCAGGAGAGG    420
 E  F  V  S  D  A  L  L  V  P  D  K  C  K  F  L  H  Q  E  R
                130                          140

ATGGATGTTTGCGAAACTCATCTTCACTGGCACACCGTCGCCAAAGAGACATGCAGTGAG    480
 M  D  V  C  E  T  H  L  H  W  H  T  V  A  K  E  T  C  S  E
                150                          160

AAGAGTACCAACTTGCATGACTACGGCATGTTGCCCTGCGGAATTGACAAGTTCCGA      540
 K  S  T  N  L  H  D  Y  G  M  L  P  C  G  I  D  K  F  R
                170                          180

GGGGTAGAGTTTGTGTGTTGCCCACTGGCTGAAGAAAGTGACAATGTGGATTCTGCTGAT    600
 G  V  E  F  V  C  C  P  L  A  E  E  S  D  N  V  D  S  A  D
                190                          200

GCGGAGGAGGATGACTCGGATGTCTGGTGGGGCGGAGCAGACACAGACTATGCAGATGGG    660
 A  E  E  D  D  S  D  V  W  W  G  G  A  D  T  D  Y  A  D  G
                210                          220
```

Figure 9C

```
AGTGAAGACAAAGTAGTAGAAGTAGCAGAGGAGAAGTGGCTGAGGTGGAAGAAGAA    720
 S  E  D  K  V  V  E  V  A  E  E  E  V  A  E  V  E  E  E
                          230                         240

GAAGCCGATGATGACGAGGACGATGAGGATGGTGATGAGGTAGAGGAAGAGGCTGAGGAA    780
 E  A  D  D  D  E  D  D  E  D  G  D  E  V  E  E  E  A  E  E
                          250                         260

CCCTACGAAGAAGCCACAGAGAACCACCAGCATTGCCACCACCACCACCACCACCACCACA    840
 P  Y  E  E  A  T  E  R  T  T  S  I  A  T  T  T  T  T  T  T
                          270                         280

GAGTCTGTGGAAGAGGTTGGTTCGAGTTCCTACAACAGCCAGTACCCCCTGATGCCCGTT    900
 E  S  V  E  E  V  V  R  V  P  T  T  A  A  S  T  P  D  A  V
                          290                         300

GACAAGTATCTCGAGACACCTGGGGATGAGAATGAACATGCCCATTTCCAGAAAGCCAAA    960
 D  K  Y  L  E  T  P  G  D  E  N  E  H  A  H  F  Q  K  A  K
                          310                         320

GAGAGGCTTGAGGCCAAGCACCGAGAGAGAATGTCCCAGGTCATGAGAGAATGGGAAGAG    1020
 E  R  L  E  A  K  H  R  E  R  M  S  Q  V  M  R  E  W  E  E
                          330                         340
```

Figure 9D

```
GCAGAACGTCAAGCAAAGAACTTGCCTAAAGCTGATAAGAAGGCAGTTATCCAGCATTTC  1080
 A  E  R  Q  A  K  N  L  P  K  A  D  K  K  A  V  I  Q  H  F
                            350                            360

CAGGAGAAAGTGGAATCTTTGGAACAGGAAGCAGCAGCCAACGAGAGACAGCAGCTGGTGGAG  1140
 Q  E  K  V  E  S  L  E  Q  E  A  A  N  E  R  Q  Q  L  V  E
                            370                            380

ACACACATGGCCAGAGTGGAAGCCATGCTCAATGACCGCCGCCTGGCCCTGGAGAAC  1200
 T  H  M  A  R  V  E  A  M  L  N  D  R  R  L  A  L  E  N
                            390                            400

TACATCACCGCTCTGCAGGCTGTTCCTCCTCGGCCTCGTCACGTGTTCAATATGCTAAAG  1260
 Y  I  T  A  L  Q  A  V  P  P  R  P  R  H  V  F  N  M  L  K
                            410                            420

AAGTATGTCCGCGCAGAACAGAAGGACAGACAGCATACACCCTAAAGCATTTCGAGCATGTG  1320
 K  Y  V  R  A  E  Q  K  D  R  Q  H  T  L  K  H  F  E  H  V
                            430                            440

CGCATGGTGGATCCCAAGAAAGCCGCTCAGATCCGTCCCAGGTTATGACACACCTCCGT  1380
 R  M  V  D  P  K  K  A  A  Q  I  R  S  Q  V  M  T  H  L  R
                            450                            460
```

Figure 9E

```
GTGATTTATGAGCGGCATGAATCAGTCTCTCTCCCTGCTCTACAACGTGCCTGCAGTGGCC  1440
 V  I  Y  E  R  M  N  Q  S  L  L  Y  N  V  P  A  V  A
                     470                              480

GAGGAGATTCAGGATGATGAAGTTGATGAGCTGCTTCAGAAAGAGCAAAACTATTCAGATGAC  1500
 E  E  I  Q  D  D  E  V  D  E  L  L  Q  K  E  Q  N  Y  S  D  D
                     490                              500

GTCTTGGCCAACATGATTAGTGAACCAAGGATCAGTTACGGAAACGATGCTCTCATGCCA  1560
 V  L  A  N  M  I  S  E  P  R  I  S  Y  G  N  D  A  L  M  P
                     510                              520

TCTTTTGACCGAAAACGAAAAACCACCGTGGAGCTCCTTCCCGTGAATGGAGAGTTCAGCCTG  1620
 S  L  T  E  K  T  T  V  E  L  L  P  V  N  G  E  F  S  L
                     530                              540

GACGATCTCCAGCCCTGGCATTCTTTTGGGGCTGACTCTGTGCCAGCCAACACAGAAAAC  1680
 D  D  L  Q  P  W  H  S  F  G  A  D  S  V  P  A  N  T  E  N
                     550                              560

GAAGTTGAGCCTGTTGATGCCCGCCCTGCTGCCGAGGACTGACCACTCGACCAGGT  1740
 E  V  E  P  V  D  A  R  P  A  A  D  R  G  L  T  T  R  P  G
                     570                              580
```

Figure 9F

```
TCTGGGTTGACAAATATCAAGAGACGGAGGAGAGATCTCTGAAGTGAAGATGGATGCAGAATTC  1800
 S  G  L  T  N  I  K  T  E  E  I  S  E  V  K  M  D  A  E  F
                      590                              600

CGACATGACTCAGGAGATATGAAGTTCATCATCAAAAATTGGTGTTCTTTGCAGAAGATGTG  1860
 R  H  D  S  G  Y  E  V  H  H  Q  K  L  V  F  F  A  E  D  V
                      610                              620

GGTTCAAACAAAGGTGCAATCATTGGACTCATGGTGGGCGGTGTGTCATAGCAGACAGTG  1920
 G  S  N  K  G  A  I  I  G  L  M  V  G  G  V  V  I  A  T  V
                      630                              640

ATCGTCATCACCTTGGTGATGCTGAAGAAGAAACAGTACACATCCATTCATCATGGTGTG  1980
 I  V  I  T  L  V  M  L  K  K  K  Q  Y  T  S  I  H  H  G  V
                      650                              660

GTGGAGGTTGACGCCGCTGTCACCCCAGAGGAGCGCCACCTGTCCAAGATGCAGCAGAAC  2040
 V  E  V  D  A  A  V  T  P  E  E  R  H  L  S  K  M  Q  Q  N
                      670                              680

GGCTACGAAAATCCAACCTACAAGTTCTTTGAGCAGATGCAGAACTAGACCCCGCCACA  2100
 G  Y  E  N  P  T  Y  K  F  F  E  Q  M  Q  N  *
                      690

GCAGCCCTCTGAAGTTGGACAGCAAAAACCATTGCTTCACTACCCATCGGTGTCCATTTATA  2160
```

Figure 9G

```
GAATAATGTGGGAAGAAACAAACCCGTTTATGATTACTCATTATCGCCTTTTGACAGC    2220
TGTGCTGTAACAAGTAGATGCCTGAACTTGAATTAATCCACACATCAGTAATGTATTC    2280
TATCTCTCTTTACATTTTGGTCTCTATACTACATTATTAATGGGTTTTGTGTACTGTAAA   2340
GAATTTAGCTGTATCAAACTAGTGCATGAATAGATTCTCTCCTGATTATTATCACATAG   2400
CCCCTTAGCCCAGTTGTATATTATTCTTGTGGTTTGTGACCCAATTAAGTCCTACTTTACA 2460
TATGCTTTAAGAATCGATGGGGATGCTTCATGTGAACGTGGGAGTTCAGCTGCTTCTCT   2520
TGCCTAAGTATTCCTTCCCTGATCACTATGCATTTAAAGTTAAACATTTTAAGTATTT    2580
CAGATGCTTTAGAGAGATTTTTTTCCATGACTGCATTTTACTGTACAGATTGCTGCTTC   2640
TGCTATATTTGTGATATAGGAATTAAGAGGATACACACGTTTGTTCTTCGTGCCTGTTT   2700
TATGTGCACACATTAGGCATTGAGACTTCAAGCTTTTCTTTTTTTGTCCACGTATCTTTG  2760
GGTCTTTGATAAAGAAAAGAATCCCTGTTCATTGTAAGCACTTTACGGGGCGGGTGGGG   2820
AGGGGTGCTCTGGTCTTCAATTACCAAGAATTCTCCAAAACAATTTCTGCAGGATG      2880
ATTGTACAGAATCATTGCTTATGACATGATGCTTTCTACACTGTATTACATAAATAAAT   2940
```

Figure 9H

TAAATAAAATAACCCCGGGCAAGACTTTTCTTTGAAGGATGACTACAGACATTAAATAAT 3000

CGAAGTAATTTTGGGTGGGGAGAAGAGGCAGATTCAATTTTCTTTAACCAGTCTGAAGTT 3060

TCATTTATGATACAAAAGAAGATGAAAAATGGAAGTGGCAATATAAGGGGATGAGGAAGC 3120

ATGCCTGGACAAACCCTTCTTTTAAGATGTGTCTTCAATTTGTATAAAATGGTGTTTCA 3180

TGTAAATAAATACATTCTTGGAGGAGC - poly(A) tail

Figure 10A

```
                                                                    GAAT    4
TCCCGGGGAGCAGCGTGCGCGGGCCCCGGGAGACGGGGTAGCGGGGGGCAGAG              64
CAAGGACGCGGGGGATCCCACTCGCACAGCAGCGCACTCGGTGCCCCGGCAGGGTCGCG       124
ATGCTGCCCGGTTTGGCACTGCTCCTGCTGGCCTGGACGGCTCGGGCGCTGGAGGTA         184
 M  L  P  G  L  A  L  L  L  L  A  W  T  A  R  A  L  E  V
 1                          10
CCCACTGATGGTAATGCTGGCCTGCTGGCTGAACCCCAGATTGCCATGTTCTGTGGCAGA      244
 P  T  D  G  N  A  G  L  L  A  E  P  Q  I  A  M  F  C  G  R
                            30
CTGAACATGCACATGAATGTCCAGAATGGGAAGTGGGATTCAGATCCATCAGGGACCAAA      304
 L  N  M  H  M  N  V  Q  N  G  K  W  D  S  D  P  S  G  T  K
                            50
ACCTGCATTGATACCAAGGAAGGCATCCTGCAGTATTGCCAAGAAGTCTACCCTGAACTG      364
 T  C  I  D  T  K  E  G  I  L  Q  Y  C  Q  E  V  Y  P  E  L
                            70
CAGATCACCAATGTGGTAGAAGCCAACCAGCCAGTGACCATCCAGAACTGGTGCAAGCGG      424
 Q  I  T  N  V  V  E  A  N  Q  P  V  T  I  Q  N  W  C  K  R
                            90
```

Figure 10B

```
GGCCGCAAGCAGTGCAAGACCCATCCCCACTTTGTGATTCCCTACCGCTGCTTAGTTGGT    484
 G  R  K  Q  C  K  T  H  P  H  F  V  I  P  Y  R  C  L  V  G
                            110

GAGTTTGTAAGTGATGCCCTTCTCGTTCCTGACAAGTGCAAATTCTTACACCAGGAGAGG    544
 E  F  V  S  D  A  L  L  V  P  D  K  C  K  F  L  H  Q  E  R
                            130

ATGGATGTTTGCGAAACTCATCTTCACTGGCACACCGTCGCCAAAGAGACATGCAGTGAG    604
 M  D  V  C  E  T  H  L  H  W  H  T  V  A  K  E  T  C  S  E
                            150

AAGAGTACCAACTTGCATGACTACGGCATGTTGCCCTGCGGAATTGACAAGTTCCGA       664
 K  S  T  N  L  H  D  Y  G  M  L  P  C  G  I  D  K  F  R
                            170

GGGGTAGAGTTTGTGTGTTGTGCCCACTGGCTGAAGAAAGTGACAATGTGGATTCTGCTGAT    724
 G  V  E  F  V  C  C  P  L  A  E  E  S  D  N  V  D  S  A  D
                            190

GCGGAGGAGGATGACTCGGATGTCGTTGGGGGCGGAGCAGAGACTATGCAGATGGG       784
 A  E  E  D  D  S  D  V  W  G  G  A  D  T  D  Y  A  D  G
                            210
```

Figure 10C

```
AGTGAAGACAAAGTAGTAGAAGAGGAAGAAGTGGCTGAGGTGGAAGAAGAA    844
 S  E  D  K  V  V  E  E  E  V  A  E  V  E  E  E
                       230
GAAGCCGATGATGACGAGGAGGATGAGGATGGTGATGAGGTAGAGGAGGCTGAGGAA    904
 E  A  D  D  D  E  D  D  E  D  G  D  E  V  E  E  A  E  E
                             250
CCCTACGAAGCCACAGAGAAGCCACCACCACCAGCATTGCCACCACCACCACCACCACA    964
 P  Y  E  A  T  E  R  T  T  S  I  A  T  T  T  T  T  T  T
                             270
GAGTCTGTGGAAGAGGTGGTTCGAGAGGTGTGCTCTGAACAAGCCGAGACGGGGCCGTGC   1024
 E  S  V  E  E  V  V  R  E  V  C  S  E  Q  A  E  T  G  P  C
                             290
CGAGCAATGATCTCCCGCTGGTACTTTGATGTGACTGAAGGAAGTGTGCCCATTCTTT   1084
 R  A  M  I  S  R  W  Y  F  D  V  T  E  G  K  C  A  P  F  F
                             310
TACGGGGGATGTGGCGGCAACCGGAACAACTTTGACACAGAAGAGTACTGCATGGCCGTG   1144
 Y  G  G  C  G  G  N  R  N  N  F  D  T  E  E  Y  C  M  A  V
                             330
```

Figure 10D

```
TGTGGCAGCGCCATTCCTACAACAGCAGCCAGTACCCCCTGATGCCGTTGACAAGTATCTC  1204
 C  G  S  A  I  P  T  T  A  A  S  T  P  D  A  V  D  K  Y  L
                      350

GAGACACCTGGGGATGAGAATGAACATGCCCATTTCCAGAAAGCCAAAGAGAGGCTTGAG   1264
 E  T  P  G  D  E  N  E  H  A  H  F  Q  K  A  K  E  R  L  E
                      370

GCCAAGCACCGAGAGAGAATGTCCCAGGTCATGAGAGAATGGGAAGAGGCAGAACGTCAA   1324
 A  K  H  R  E  R  M  S  Q  V  M  R  E  W  E  E  A  E  R  Q
                      390

GCAAAGAACTTGCCTAAAGCTGATAAGAAGGCAGTTATCCAGCATTTCCAGGAGAAAGTG   1384
 A  K  N  L  P  K  A  D  K  K  A  V  I  Q  H  F  Q  E  K  V
                      410

GAATCTTTGGAACAGGAAGCAGCAGCCAACGAGAGACAGCAGCTGGTGGAGACACATGGCC  1444
 E  S  L  E  Q  E  A  A  A  N  E  R  Q  Q  L  V  E  T  H  M  A
                      430

AGAGTGGAAGCCATGCTCAATGACCGCCGCCTGGCCCTGGAGAACTACATCACCGCT     1504
 R  V  E  A  M  L  N  D  R  R  L  A  L  E  N  Y  I  T  A
                      450
```

Figure 10E

```
CTGCAGGCTGTGTTCCTCGGCCTCGTCACGTGTTCAATATGCTAAAGAAGTATGTCCGC  1564
 L  Q  A  V  P  P  R  H  V  F  N  M  L  K  K  Y  V  R
                        470

GCAGAACAGAAGGAGACAGAGCACACCTAAAGCATTTCGAGCATGTGCGCATGGTGGAT  1624
 A  E  Q  K  D  R  Q  H  T  L  K  H  F  E  H  V  R  M  V  D
                        490

CCCAAGAAAGCCGCTCAGATCCGGTCCCAGGTTATGACACACCTCCGTGTGATTTATGAG  1684
 P  K  K  A  A  Q  I  R  S  Q  V  M  T  H  L  R  V  I  Y  E
                        510

CGCATGAATCAGTCTCTCCCCTGCTCTTATACAACGTGCCTGCAGTGGCCGAGGAGATTCAG  1744
 R  M  N  Q  S  L  L  Y  N  V  P  A  V  A  E  E  I  Q
                        530

GATGAAGTTGATGAGCTGCTTCAGAAAGAGCAAAACTATTCAGATGACGTCTTGGCCAAC  1804
 D  E  V  D  E  L  L  Q  K  E  Q  N  Y  S  D  D  V  L  A  N
                        550

ATGATTAGTGAACCAAGGATCAGTTACGGAAACGATGCTCTCATGCCATCTTTGACCGAA  1864
 M  I  S  E  P  R  I  S  Y  G  N  D  A  L  M  P  S  L  T  E
                        570
```

Figure 10F

```
ACGAAAACCACCGTGGAGCTCCTTCCCGTGAATGGAGAGTTCAGCCTGGACGATCTCCAG  1924
 T  K  T  T  V  E  L  L  P  V  N  G  E  F  S  L  D  D  L  Q
                          590

CCGTGGCATTCTTTTGGGCTGACTCTGTGCCAGCCAACACAGAAAACGAAGTTGAGCCT   1984
 P  W  H  S  F  G  A  D  S  V  P  A  N  T  E  N  E  V  E  P
                          610

GTTGATGCCCGCCCTGCTGCCGACCGAGGACTGACCACTCGACCAGGTTCTGGGTTGACA  2044
 V  D  A  R  P  A  A  D  R  G  L  T  T  R  P  G  S  G  L  T
                          630

AATATCAAGACGGAGGAGATCTCTGAAGTGAAGATGGATGCAGAATTCCGACATGACTCA  2104
 N  I  K  T  E  E  I  S  E  V  K  M  D  A  E  F  R  H  D  S
                          650

GGATATGAAGTTCATCATCAAAAATTGGTGTTCTTTGCAGAAGATGTGGGTTCAAACAAA  2164
 G  Y  E  V  H  H  Q  K  L  V  F  F  A  E  D  V  G  S  N  K
                          670

GGTGCAATCATTGGACTCATGGTGGGCGGTGTTGTCATAGCGACAGTGATCGTCATCACC  2224
 G  A  I  I  G  L  M  V  G  G  V  V  I  A  T  V  I  V  I  T
                          690
```

Figure 10G

```
TTGGTGATGCTGAAGAAGAAACAGTACACATTCATTCATGGTGTGGTGGAGGTTGAC  2284
 L  V  M  L  K  K  K  Q  Y  T  S  I  H  H  G  V  V  E  V  D
                              710

GCCGCTGTCACCCCAGAGGAGCGCCACCTGTCCAAGATGCAGCAGAACGGCTACGAAAAT  2344
 A  A  V  T  P  E  E  R  H  L  S  K  M  Q  Q  N  G  Y  E  N
                              730

CCAACCTACAAGTTCTTTGAGCAGATGCAGAACTAGACCCCGCCACAGCAGCCTCTGAA  2404
 P  T  Y  K  F  F  E  Q  M  Q  N
                   750

GTTGGACAGCAAAACCATTGCTTCACTACCCATCGGTGTCCATTTATAGAATAATGTGGG  2464

AAGAAACAAACCCGTTTTATGATTTACTCATTATCGCCTTTTGACAGCTGTGCTGTAACA  2524

CAAGTAGATGCCTGAACTTGAATTAATCCACACATCAGTAATGTATTCTATCTCTCTTTA  2584

CATTTTGGTCTCTATACTACACATTATTAATGGGTTTTGTGTACTGTAAAGAATTAGCTGT  2644

ATCAAACTAGTGCATGAATAGATTCTCCCTGATTATTTATCACATAGCCCCTTAGCCAG  2704

TTGTATATTATTCTTGTGGTTTGTGACCCAATTAAGTCCTACTTTACATATGCTTTAAGA  2764

ATCGATGGGGATGCTTCATGTGAACGTGGGAGTTCAGCTGCTTCTCTTGCCTAAGTATT  2824
```

Figure 10H

```
CCTTTCCTGATCACTATGCATTTTAAAGTTAAACATTTTTAAGTATTTCAGATGCTTTAG  2884
AGAGATTTTTTCCATGACTGCATTTTACTGTACAGATTGCTGCTTCTGCTATATTTGT    2944
GATATAGGAATTAAGAGGATACACACGTTTGTTCTTCGTGCCTGTTTTATGTGCACACA   3004
TTAGGCATTGAGACTTCAAGCTTTTCTTTTTTGTCCACGTATCTTTGGGTCTTTGATAA   3064
AGAAAAGAATCCCTGTTCATTGTAAGCACTTTTACGGGCGGTGGGGAGGGTGCTCTG     3124
CTGGTCTTCAATTACCAAGAATTC
```

Figure 11B

```
1                                                                                                    864
ATGCTGCCCGGT ─────────────────────────────────────────────────────────────────────── GTTCGA
MetLeuProGly                                                                          ValArg
  1                                                                                      288

865▼          880              900              920
GAGGTGTGCTCTGAACAAGCCGAGACGGGGCCCGTGCCGAGCAATGATCTCCCGCTGGTAC
GluValCysSerGluGlnAlaGluThrGlyProCysArgAlaMetIleSerArgTrpTyr
  289                                                                                    308

940              960              980
TTTGATGTGACTGAAGGGAAGTGTGCCCCATTCTTTTACGGCGGATGTGGCGGCAACCGG
PheAspValThrGluGlyLysCysAlaProPhePheTyrGlyGlyCysGlyGlyAsnArg
                                                                                         328

1000             1020             1040
AACAACTTTGACACAGAAGAGTACTGCATGGCTGTGTGTGGCAGCGGCCATGTCCAAAGT
AsnAsnPheAspThrGluGluTyrCysMetAlaValCysGlySerAlaMetSerGlnSer
                                                                                         348

1060             1080             1090▼
TTACTCAAGACTACCCAGGAACCCTCTTGCCCGAGATCCTGTTAAACTTCCTACAACA ───
LeuLeuLysThrThrGlnGluProLeuAlaArgAspProValLysLeuProThrThr
                                                                                         364
```

Figure 12A.

SPLICING ACCEPTOR SITE

INTRON

5'                                                                                                      3'

1  TGATAGTTATCCCTGTTCTTCCTCCAAGCCCTCTGCCTTGG
   AGCTATGGATACTATAACTAACTGAAGCTTCTTCTTTCAG

2  ACAGTGGAGGCTTGTTAGATGCTTGTAAATGCCAGCCCCT
   GCCTCAAGTAACAATTGATTCTTTTGTGTGCTCTCCCAG

3  TCTATCTTTCCTTGATGTCTTCTGCGGTAAGAACACTGTG
   ATACAGATGGAATGACGGAAGTGGTTTTCCTTTCTTTCAG

4  TTGATTATTTATGCGGAGTTTCTTAAAATGAAACACAT
   CATCTCTAGCCACTCACTGTTTCTCCTTACACTTTGTAG

5  AAAATTCCATATGGACGACTTTTCTTTTCCTTCCCT
   GAAATGTGGTTTAATTGACTTTTTCTGTTTGCCTTCACAG

6  AAGAAGTAAACGTGTATACATGAACAGAGAGACAGTGCCT
   TTTCATGCTAAAATGTGGTTCCCCACATCTCCTCTGATTAG

7  GTCAGTGGACTCGTGCATTTCACCATCATTCCCATGTTTC
   TCTTTTTGTTTTTTAGTTATGTTCTTATTTTTTCCATAG

8  ATACGGCTTTCTATTAAACGAGTGGATTATTCTGTTGTTG
   TTGGCTTTTTTTCTCAAACCCTCCTTCTCTTACTTTATAG

Figure 12B

9  ACATAATCATCATCCTATTAAGTCTGTATTCAAAGGATG
   AACTGATGATTTTAAATTCAAATGTTTCCTTAATTATAG

10 ATGTCTTTTTTAGAAGACTTGAAATTGCTGCTTCATCCTA
   CTTATTCAGTCCCCATGGACATATGTGTTTATGATGGCAG

11 TGGAACCTCTAACCATCGCCAATGGAAGAAGCAGTGTTT
   GCACAAACTTGAAAAGAGTTTTCATTTTCCTCCCACAG

12 AAAAAAAAAGAAAAAAGAAAAAGAAAAAGAACCATTCCT
   ACCCCCAGACATGTGACCTGGAGTGTCATCCTTGATGCAG

13 CAGAAGTAAATGGTGGCTGCTGCTGCTGCTGTTGTGA
   TTGTTGTTACTCACCAAAGAGATGGTTTTGTTTGGTTTAG

14 CGACTATGTTTGGGAGCCACGACTTACCGATCTTGATTTG
   TCTTGATTGGCTTTCTGTCCCTGGCTTGCCTGTGCCAG

15 TAGGCTTTGTCTTACAGTGTTATTATTATGAGTAAAACT
   AATTGGTGTCCTGCATACTTTAATTTATGATGTAATACAG

16 AATTCTTCTAATTGCGTTTATAAATTGTAAATTATATTGC
   ATTTAGAAATTAAAATTATTTTCTTAATTTGTTTTCAAG

17 TTATCTTTTACTGCTTCTCCATGTTCACCCTTAAAAGAA
   TGAATTTTATTTTTTTACTCAGCTCTCCTCCTGTTTTCAG

Figure 12C

| EXON | | SPLICING DONOR SITE |
|---|---|---|
| | 5' | 3' |
| EXON1 (-146-+57:203nt) | ...GGGCGCTGGAG | GTGGGTGCCGCGCCTCGGAA |
| EXON2 (58-225:168nt) GTACCCACTG... | TTGCCAAGAA | GTAAGTCCTGTCCGGTGGCT |
| EXON3 (226-355:130nt) GTCTACCCTG... | CGCTGCTTAG | GTGAGCCCGGCCCGAGGG |
| EXON4 (356-468:113nt) TTGGTGAGTT... | TGCCAAAGAG | GTACC |
| EXON5 (469-662:194nt) ACATGCAGTG... | CAGATGGGAG | GTAAGGTGGCATGAATTCCG |
| EXON6 (663-865:203nt) TGAAGACAAA... | GTGGTTCGAG | GTAATCCACCATTTGCTTGG |
| EXON7 (866-1033:168nt) AGGTGTGCTC... | GGCAGCGCCA | GTAAGTGGACCCTTCTTCGA |
| EXON8 (1033-1090:57nt) TGTCCCAAAG... | CCTGTTAAAC | GTACGCGATCACTGAGGAGG |
| EXON9 (1091-1224:134nt) TTCCTACAAC... | AATGTCCCAG | GTAAGTCTGCTCTTCCATCA |

Figure 12D

EXON10 (1225-1299:75nt)
GTCATGAGAG..... AGTTATCCAG GTAAAACCTGAACCCATTTC

EXON11 (1300-1458:159nt)
CATTTCCAGG..... TCCTCCTCGG GTAGGTCTCGCTGCAGCCGA

EXON12 (1459-1587:129nt)
CCTCGTCACG..... CCGGTCCCAG GTAAGCGTGGGGTATAATCA

EXON13 (1588-1687:100nt)
GTTATGACAC..... GATGAAGTTG GTAAGTAAGTGTTCTTTTGA

EXON14 (1688-1909:222nt)
ATGAGCTGCT..... GAAAACGAAG GTAAGAGTCCCCCTGAGCCAG

EXON15 (1910-1963:54nt)
TTGAGCCTGT..... ACTCGACCAG GTATCAGAACCGCTTGACGT

EXON16 (1964-2064:101nt)
GTTCTGGGTT..... TCAAAAATTG GTACGTAAAATAATTACCCT

EXON17 (2065-2211:147nt)
GTGTTCTTTG..... TGTGGTGGAG GTAGGTAAACTTGACTGCAT

EXON18 (2212-3432:1221nt)
GTTACGCCGC..... TTGGAGGAGC

Figure 13 ccaaatgtcccgtcattaagaaatgaaattctctaattgcgttataaattgta aattatattgcatttagaattaaaattcttttcttaatttgtttcaag GTG TTC TTT
                                                  Val Phe Phe GCA GAT GTG GGT TCA AAC AAA GGT GCA ATC ATT GGA CTC ATG GTG
Ala Glu Asp Val Gly Ser Asn Lys Gly Ala Ile Ile Gly Leu Met Val T
GGC GGT GTT GTC ATA GCG ACA GTG ATC GTC ATC ACC TTG GTG ATG CTG
Gly Gly Val Val Ile Ala Thr Val Ile Val Ile Thr Leu Val Met Leu
                                        Phe AAG AAA CAG TAC ACA TCC ATT CAT CAT GGT GTG GTG GAG gtaggtaaac
Lys Lys Lys Gln Tyr Thr Ser Ile His His Gly Val Val Glu ttgactgcat gtttccaagt gggaattaag actatgagag

CDNA-GENOMIC DNA HYBRID SEQUENCE ENCODING APP770 CONTAINING A GENOMIC DNA INSERT OF THE KI AND OX-2 REGIONS

This is a continuation of application Ser. No. 07/817,584 filed on Jan. 7, 1992 now abandoned, by Samuel Wadsworth, Benjamin Snyder, Vermuri B. Reddy and Chamer Wei.

BACKGROUND OF THE INVENTION

Transgenic technology is described for the production of animals that exhibit symptoms of human Alzheimer's disease through the expression of the Alzheimer's precursor protein or a modified version thereof.

Alzheimer's Disease (AD) is a degenerative disorder of the brain first described by Alios Alzheimer in 1907 after examining one of his patients who suffered drastic reduction in cognitive abilities and had generalized dementia ("The early story of Alzheimer's Disease", edited by Bick K, Amaducci L, and Pepeu G. (Raven Press, New York 1987). It is the leading cause of dementia in elderly persons. AD patients have increased problems with memory loss and intellectual functions which progress to the point where they cannot function as normal individuals. With the loss of intellectual skills the patients exhibit personality changes, socially inappropriate actions and schizophrenia ("A guide to the understanding of Alzheimer's Disease and related disorders", edited by Jorm AF.; (New York University Press, New York 1987). AD is devastating for both victims and their families, for there is no effective palliative or preventive treatment for the inevitable neurodegeneration. The most common problems in the Alzheimer's patient are inability to dress unaided, restlessness by day, urinary incontinence and sleep disturbances. The family members report embarrassment, anxiety, depression, and a decreased social life.

The impact of AD on society and on the national economy is enormous. It is expected that the demented elderly population in the United States will increase by 41% by the year 2000. It is expensive for the health care systems that must provide institutional and ancillary care for the patients at an estimated annual cost of $40 billion (Jorm, 1987; Fisher, LM: New York Times, Aug. 23, 1989 D1 "Alzheimer's Disease", edited by Reisberg, B.; (The Free Press, New York & London 1983). These factors imply preventive action must be taken to decrease AD incidence by allocating resources into AD research.

At a macroscopic level, the brains of AD patients are usually smaller, sometimes weighing less than 1,000 grams. At a microscopic level, the histopathological symptoms of AD include neurofibrillary tangles (NFT), neuritic plaques, and degeneration of neurons. AD patients exhibit degeneration of nerve cells in the frontal and temporal cortex of the cerebral cortex, pyramidal neurons of hippocampus, neurons in the medial, medial central, and cortical nuclei of the amygdala, noradrenergic neurons in the locus coeruleus, and the neurons in the basal forebrain cholinergic system. Loss of neurons in the cholinergic system leads to a consistent deficit in cholinergic presynaptic markers in AD (Reisberg, 1983; "Alzheimer's Disease and related disorders, research and development" edited by Kelly WE; (Charles C. Thomas, Springfield, Ill. 1984).

AD is associated with neuritic plaques measuring up to 200 µm in diameter in the cortex, hippocampus, subiculum, hippocampal gyrus, and amygdala. One of the principal constituents of neuritic plaques is amyloid, which is stained by congo red (Reisberg, 1983; Kelly, 1984). Amyloid plaques are extracellular, pink- or rust-colored in bright field, and birefringent in polarized light. The plaques are composed of polypeptide fibrils and are often present around blood vessels, reducing blood supply to various neurons in the brain.

Various factors such as genetic predisposition, infectious agents, toxins, metals, and head trauma have all been suggested as possible mechanisms of AD neuropathy. However, available evidence strongly indicates two distinct types of genetic predisposition for AD. First, molecular analysis has provided evidence for mutations in the amyloid precursor protein (APP) gene in certain AD-stricken families (Goate, et al. *Nature* 349:704–706 (1991); Murrell, J, et al. *Science* 254; 97–99, 1991; Chartier-Harlin, M-C, et al. *Nature* 353, 844–846 (1991)). Second, in certain other families with a clear genetic predisposition to AD, the mutation maps to chromosome 21 but is distinct from the APP locus (Tanzi, R. E., et al. *Nature*, 331;528–530 (1988)).

Amyloid plaques are abundantly present in AD patients and in Down's Syndrome individuals surviving to the age of 40. The plaques are also present in the normal aging brain, although at a lower number. These plaques are made up of the amyloid β peptide (β peptide) (Glenner and Wong, et al., *Biochem. Biophys. Res. Comm.* 120:885–890 (1984)), which is also the main protein constituent in cerebrovascular deposits and neurofibrillary tangles. The peptide is a filamentous material that is arranged in beta-pleated sheets and has a molecular weight of 4.2–4.5 kd. It is a hydrophobic peptide comprising 39–42 amino acids. The determination of its amino acid sequence led to the cloning of the APP cDNA (Kang, et al., *Nature* 325:733–735 (1987); Goldgaber, et al., *Science* 235:877–880 (1987); Robakis et al., *Proc. Natl. Acad. Sci.* 84:4190–4194 (1987); Tanzi, et al., *Nature* 331:528–530 (1988) and genomic APP DNA (Lemaire et al., *Nucl. Acids Res.* 17:517–522 (1989); Yoshikai, et al., *Gene* 87, 257–263 (1990). Three forms of APP cDNAs (APP695, APP751, and APP770) have been isolated, and arise from a single precursor RNA by alternate splicing. The gene spans more than 175 Kb with 18 exons (Yoshikai, et al., 1990). APP contains three extracellular domains, a transmembrane region and a cytoplasmic domain. The β peptide consists of 28 amino acids just outside the membrane and 14 residues of the hydrophobic transmembrane domain. Thus, the β peptide is a cleavage product of APP normally found in brain and other tissues such as heart, kidney and spleen. β peptide deposits, however, are usually found only in the brain, although Joachim et al., *Nature* 341:226–228 (1989) have reported β peptide deposits outside the brain in the skin, intestine, and subcutaneous tissues of most AD patients.

The larger alternate forms of APP (APP751, APP770) consist of all of APP695 plus one or two additional domains. APP751 consists of all of APP695 plus an additional 56 amino acids which has homology to the Kunitz family of serine protease inhibitors (KP1) (Tanzi et al., 1988; Weidemann, et al., *Cell* 57:115–126 (1989); Kitaguchi, et al., *Nature* 331:530–532 (1988); Tanzi et al., *Nature* 329, 156 (1987). APP770 contains APP751 and an additional 19 amino acid domain homologous to the neuron cell surface antigen OX-2 (Weidemann, et al., *Cell* 57:115–126 (1989); Kitaguchi et al., 1988). APP is posttranslationally modified by the removal of the leader sequence and by the addition of sulfate and sugar groups.

Van Broeckhaven, et al., *Science* 248:1120–1122 (1990) have demonstrated that the APP gene is tightly linked to hereditary cerebral hemorrhage with amyloidosis (HCHWA-D) in two Dutch families. This was confirmed by the finding of a point mutation in the APP coding region in two Dutch patients (Levy et al., *Science* 248:1124–1128 (1990). The mutation substituted a glutamine for glutamic acid at position 22 of the β peptide (position 618 of APP695). In addition, certain families are genetically predisposed to Alzheimer's disease, a condition referred to as familial Alzheimer's disease (FAD), through mutations resulting in an amino acid replacement at position 717 of the full length protein (Goate, et al., (1991); Murrell et al., 1991; Chartier-Harlin et al., 1991). These mutations co-segregate with the disease within the families and are absent in families with late-onset AD.

There are no proven animal models to study AD, although aging nonhuman primates seem to develop amyloid plaques of β peptide in brain parenchyma and in the walls of some meningeal and cortical vessels. Although aged primates and canines can serve as animal models, they are expensive to maintain and need lengthy study periods. There are no spontaneous animal mutations with sufficient similarities to AD to be useful as experimental models. Various models have been proposed in which some AD-like symptoms may be induced by electrolysis, transplantation of AD brain samples, aluminum chloride, kainic acid or choline analogs (Kisner, et al., *Neurobiol Aging* 7;287–292 (1986); Mistry, J. S., et al., *J Med Chem* 29;337–343 (1986)). Flood, et al. (*Proc. Natl. Acad. Sci.* 88:3363–3366 (1986), reported amnestic effects in mice of four synthetic peptides homologous to the B peptide. Because none of these share with AD either common symptoms, biochemistry or pathogenesis, they are not likely to yield much useful information on etiology or treatment.

Transgenic mice with the human APP promoter linked to *E. coli* β-galactosidase (Wirak, D. O., et al., *The EMBO J* 10;289–296 (1991)) as well as transgenic mice expressing the human APP751 cDNA (Quon, D, et al. *Nature* 352, 239–241 (1991)) or subfragment of the cDNA including the β peptide (Wirak, D. O., et al., *Science* 253, 323–325 (1991); Sandhu, F. A., et al., *J. Biol. Chem.* 266, 21331–21334 (1991); Kawabata, S. *Nature* 354, 476–478 (1991)) have been produced. Results obtained in the different studies appear to depend upon the source of promoter and the protein coding sequence used. For example, Wirak, et al. (1991) found that in transgenic mice expressing a form of the β peptide, intracellular deposits of "amyloid-like" material, reactive with antibodies prepared against APP were observed but did not find other histopathological disease symptoms. The intracellular nature of the antibody-reactive material and the lack of other symptoms suggest that this particular transgenic animal is not a faithful model system for Alzheimer's disease. Kawabata et al. (1991) report the production of amyloid plaques, neurofibrillary tangles, and neuronal cell death in their transgenic animals. In each of these studies, the same peptide fragment, the β peptide plus the 56 remaining C terminal amino acids of APP, was expressed. Wirak et al. (1991) used the human APP promoter while Kawabata, et al. (1991) used the human thy-1 promoter. In transgenic mice expressing the APP751 cDNA from the neuron-specific enolase promoter of Quon, D., et al., *Nature* 352, 239–241 (1991), extracellular deposits of material reactive with antibody prepared against APP were observed. What was not shown was whether the deposits contained full-length APP751 or β peptide or both, thus precluding any correlation of the deposits with those present in Alzheimer's disease. Quon et al. (1991) also state that the protein encoded by the APP695 cDNA expressed from the neuron-specific enolase promoter, does not form extracellular immunoreactive deposits. These results raise the possibility that although the B peptide is included within the APP695 precursor, use of the neuron-specific enolase promoter in conjunction with the APP695 cDNA may not present an effective Alzheimer's disease model. Furthermore, the presence of APP immunoreactive deposits is not correlated with the age or gene dosage in their particular transgenic model.

Alzheimer's disease is a complex syndrome involving pathological and behavioral aspects. A useful disease model should take these complexities into account. There are multiple proteins expressed from the gene with certain forms predominating in a given tissue. In the brain, the 695 form is predominant, but the mRNAs for additional forms are also present (Golde et al., *Neuron* 4; 253–267 (1990)). It is not known whether the ratio of the different forms changes with the age of the individual. The various protein forms result from alternative splicing such that the KI domain and/or the OX-2 domain may or may not be present in the mature protein. Moreover, the β-peptide results from post-translational processing of the precursor protein. This process can change in time as an individual ages, and can be affected by mutations not directly affecting the structure of the β-peptide: for example, the familial Alzheimer's disease (FAD) mutations at amino acid position 717 in the full length protein (Groate, et al., 1991; Murrell, et al., 1991; Chartier-Harlin, et al., 1991). Given these considerations, the production of universal animal models for Alzheimer's disease necessitates the construction of animal models that take into account the effects of known mutations on the phenotype resulting from the expression of these forms, and the possibility of the ratio of the different forms changing during the lifetime of the animal.

It is therefore an object of the present invention to provide an animal model for Alzheimer's disease that is constructed using transgenic technology.

It is a further object of the present invention to provide transgenic animals that accurately reflect the expression of different forms of the amyloid precursor protein.

It is a still further object of the present invention to provide transgenic animals characterized by certain genetic abnormalities in the expression of the amyloid precursor protein.

SUMMARY OF THE INVENTION

The construction of transgenic animal models for testing potential treatments for Alzheimer's disease is described. The models are characterized by a greater similarity to the conditions existing in naturally occurring Alzheimer's disease, based on the ability to control expression of one or more of the three forms of the β-amyloid precursor protein (APP), APP695, APP751, and APP770, or subfragments thereof, as well as various point mutations based on naturally occurring mutations, such as the FAD mutations at amino acid 717, and predicted mutations in the APP gene. The APP gene constructs are prepared using the naturally occurring APP promoter of human, mouse, or rat origin, as well as inducible promoters such as the mouse metallothionine promoter, which can be regulated by addition of heavy metals such as zinc to the animal's water or diet. Neuron-specific expression of constructs is achieved by using the rat neuron specific enolase promoter.

The constructs are introduced into animal embryos using standard techniques such as microinjection or embryonic stem cells. Cell culture based models can also be prepared by two methods. Cell cultures can be isolated from the transgenic animals or prepared from established cell cultures using the same constructs with standard cell transfection techniques.

The specific constructs that are described employ the following protein coding sequences: the APP770 cDNA; the APP770 cDNA bearing a mutation at amino acid 717; the APP751 cDNA containing the KI protease inhibitor domain without the OX2 domain in the construct; the APP751 cDNA and bearing a mutation at amino acid 717; the APP695 cDNA; the APP695 cDNA bearing a mutation at amino acid 717; the APP leader sequence followed by the β peptide region plus the remaining carboxyterminal 56 amino acids of APP; the APP leader sequence followed by the β peptide region plus the remaining carboxyterminal 56 amino acids with the addition of a mutation at amino acid 717; the APP leader sequence followed by the β peptide region; the β peptide region plus the remaining carboxyterminal 56 amino acids of APP; the β peptide region plus the remaining carboxyterminal 56 amino acids of APP with the addition of a mutation at amino acid 717; a combination genomic-cDNA APP gene construct; and a combination genomic-cDNA APP gene construct, with the addition of a mutation at amino acid 717, operably linked to promoters selected from the following: the human APP promoter, mouse APP promoter, rat APP promoter, metallothionine promoter, and rat neuron specific enolase promoter. Additional constructs include a human yeast artificial chromosome construct controlled by the human APP promoter; a human yeast artificial chromosome construct controlled by the human APP promoter with the addition of a mutation at amino acid 717; the endogenous mouse or rat APP gene modified through the process of homologous recombination between the APP gene in a mouse or rat embryonic stem (ES) cell and a vector carrying the human APP cDNA of the wild-type such that sequences in the resident rodent chromosomal APP gene beyond the recombination point (the preferred site for recombination is within APP exon 9) are replaced by the analogous human sequences; the endogenous mouse or rat APP gene modified through the process of homologous recombination between the APP gene in a mouse or rat ES cell and a vector carrying the human APP cDNA bearing a mutation at amino acid position 717 such that sequences in the resident rodent chromosomal APP gene beyond the recombination point (the preferred site for recombination is within APP exon 9) are replaced by the analogous human sequences bearing a mutation at amino acid 717. These constructs can be introduced into the transgenic animals and then combined by mating of animals expressing the different constructs.

The transgenic animals, or animal cells, are used to screen for compounds altering the pathological course of Alzheimer's Disease as measured by their effect on the amount and histopathology of APP and B peptide in the animals, as well as by behavioral alterations.

BRIEF DESCRIPTION OF THE DRAWINGS

The boxed portions of the drawings indicate the amino acid coding portions of the constructs. Filled portions indicate the various domains of the protein as indicated in the Figure Legend. Lines indicate sequences in the clones that are 5' or 3' untranslated sequences, flanking genomic sequences, or introns. The break in the line to the left of the constructs in FIGS. 7 and 8 indicates the presence of a long DNA sequence.

FIG. 1a is a schematic of the APP770 cDNA coding sequence.

FIG. 1b is a schematic of the APP770 cDNA coding sequence bearing a mutation at position 717.

FIG. 2a is a schematic of the APP751 cDNA coding sequence.

FIG. 2b is a schematic of the APP751 cDNA coding sequence bearing a mutation at position 717.

FIG. 3a is a schematic of the APP695 coding sequence.

FIG. 3b is a schematic of the APP695 cDNA coding sequence bearing a mutation at position 717.

FIG. 7a is a schematic of a human APP YAC coding sequence.

FIG. 7b is a schematic of a human APP YAC coding sequence bearing a mutation at position 717.

FIGS. 8a and 8b are schematic of genetic alteration of the mouse APP gene by homologous recombination between the mouse APP gene in a mouse ES cell and a vector carrying the human APP cDNA (either of the wild-type (FIG. 8a) or FAD mutant form) (FIG. 8b) directed to the exon 9 portion of the gene. As a result of this recombination event, sequences in the resident mouse chromosomal APP gene beyond the recombination point in exon 9 are replaced by the analogous human sequences.

FIGS. 9A through 9H depict FIG. 1 of Kang, et al. (1987), showing the nucleotide sequence (SEQ ID NO:1) and predicted amino-acid sequence (SEQ ID NO:2) of a cDNA clone encoding the precursor of the amyloid A4 protein of Alzheimer's disease. Nucleotide residues are numbered in the 5' to 3' direction, beginning with the first base of the initiation codon AUG. The untranslated sequence directly following the poly(G) tail is indicated by negative numbers. The sequence shows a 695-residue open reading frame. The deduced amino-acid sequence is numbered, the amino-terminal methionine included. The amino-acid sequence of the A4 polypeptide is boxed. The synthetic oligonucleotide mixture used as a probe is indicated as a line above the corresponding cDNA. Polyadenylation signals are underlined. Nucleotide 3207 is followed by a poly(dA) tail linked to the vector DNA. The entire cDNA insert includes 3,353 bp and EcoRI sites at bp positions 1,795 and 2,851. The amino-acid composition of the 695-residue A4 precursor is A57, C12, D47, E85, F17, G31, H25, I23, K38, L52, M21, N28, P31, Q33, R33, S30, T45 resulting in a calculated $M_r$ of 78,644.45.

FIGS. 10A through 10H depict FIG. 2 of Ponte, et al. (1988), showing the nucleotide sequence (SEQ ID NO:3) and deduced 751 amino-acid sequence (SEQ ID NO:4) of the A4$_{751}$ cDNA. Numbering of nucleotides begins with the first base of the clone and proceeds in a 5' to 3' direction for a total of 3,148 bases. The inserted 167 bp domain is boxed (nucleotides 990–1,157); the insert-specific oligonucleotide (nucleotides 1,032–1,091) and deletion-specific oligonucleotide (nucleotides 975–989 plus 1,158–1,172) are underlined in bold; oligonucleotides used in cDNA isolation are underlined (nucleotides 125–167 and 1,930–1,972).

FIGS. 11A and 11B are FIGS. 1b and 1c of Kitaguchi, et al., (1988). FIG. 11A is the proposed domain structure of APP695 and APP770. Domains: 1, signal sequence; 2, cysteine-rich region; 3, highly-negatively-charged region, with novel insert (closed box) in APP770; 4, N-glycosylation-site region; 5, transmembrane segment; 6, cytoplasmic domain. Hatched box, amyloid deposited in the brain. FIG. 11B is the nucleotide sequence (SEQ ID NO:5 and SEQ ID NO:7) and predicted amino-acid sequence (SEQ ID NO:6 and SEQ ID NO:8) of the novel insert of pAPP770. The novel insert begins at nt 866 and ends at nt 1,090 (between arrowheads). The deduced amino acid sequence is numbered beginning with the amino-terminal methionine. The amino acid residues absent in APP695 are numbers 289–364.

FIGS. 12A through 12D depict FIG. 3 from Yoshikai, et al., (1990), showing the exon-intron boundaries of the BPP gene. Only the sequences from 80 nt downstream to 20 nt upstream of the exon-intron junctions are shown. The numbering of the nt of the exons is referred to Kang, et al. (1987) and Kitaguchi, et al. (1988). The nt+1 is the tsp. The nt number and size of each exon are also shown in parenthesis. Putative branchpoint sequences in the introns are underlined. The depicted nucleotide sequences of the intron-exon junctions at the splicing acceptor sites for introns 1 through 17 and exons 2 through 18, respectively, are set forth consecutively as SEQ ID NO:9 through SEQ ID NO: 25. The depicted nucleotide sequences of the exon-intron junctions at the splicing donor sites for exons 1 through 17 and introns 1 through 17, respectively, are set forth consecutively as SEQ ID NO:26 through SEQ ID NO:42. The end of exon 18 is set forth as SEQ ID NO:43.

FIG. 13 is FIG. 1 from Murrell, et al. (1991), showing the DNA sequence (SEQ ID NO:44) of nucleotides 1732 through 2036, including exon 15 of the APP gene, isolated by PCR. Lowercase letters designate introns; capital letters designate exon 15, which encodes the carboxyl-terminal portion of amyloid β protein, amino acids 614 through 669 (SEQ ID NO:45), (exon 17 if numbered by the APP770 transcript (Yoshikai, 1990). Solid lines indicate oligonucleotide primers used in the PCR reactions. The mutation at position 1924 is in the box. Solid arrowhead indicates the carboxyl terminus of the longest β-amyloid protein sequence that has been reported (43 residues).

DETAILED DESCRIPTION OF THE INVENTION

The constructs and transgenic animals and animal cells are prepared using the methods and materials described below.

Sources of Materials

Restriction endonucleases are obtained from conventional commercial sources such as New England Biolabs (Beverly, Mass.), Promega Biological Research Products (Madison, Wis.), and Stratagene (LaJolla, Calif.), etc. Radioactive materials are obtained from conventional commercial sources such as Dupont/NEN or Amersham. Custom-designed oligonucleotides for site-directed mutagenesis are available from any of several commercial providers of such materials such as Bio-Synthesis Inc., Lewisville, Tex. Kits for carrying out site-directed mutagenesis are available from commercial suppliers such as Promega Biological Research Products, Stratagene, etc. Clones of cDNA including the APP695, APP751, and APP770 forms of APP mRNA were obtained directly from Dr. Dmitry Goldgaber, NIH. Libraries of DNA are available from commercial providers such as Stratagene, La Jolla, Calif., or Clontech, Palo Alto, Calif. PC12 and 3T3 cells were obtained from ATCC (#CRL1721 and #CCL92 respectively). An additional PC12 cell line was obtained from Dr. Charles Marotta of Harvard Medical School, Massachusetts General Hospital, and McLean Hospital. Standard cell culture media appropriate to the cell line are obtained from conventional commercial sources such as Gibco/BRL. Murine stem cells, strain D3, were obtained from Dr. Rolf Kemler (Doetschman, et al., *J. Embryol. Exp. Morphol.* 87, 27 (1985)). Lipofectin for DNA transfection and the drug G418 for selection of stable transformants are available from Gibco/BRL.

Isolation of the Human APP Promoter

A cosmid library, constructed from human placental DNA in the pWE15 cosmid vector, was screened by hybridization with a $^{32}$P-labeled probe prepared by nick-translation (Maniatis, et al. *Molecular Cloning: a laboratory manual* (Cold Spring Harbor Laboratory, Cold Spring Harbor, N.Y. 1989)) of the APP770 cDNA clone. Clones that hybridized with the probe were picked, purified, and characterized by restriction mapping, hybridization, and DNA sequencing. From one such clone containing a long 5' flanking region, a NotI to NruI restriction DNA fragment of approximately 25 kb was isolated. This fragment terminates 2 nucleotides before the initiator methionine codon of the Alzheimer's protein-coding region. This fragment, or a subfragment thereof, is the source of the human APP promoter for the constructs described herein. Analogous DNA fragments isolated using the same methods from mouse or rat genomic libraries are the source of mouse or rat promoters.

Definition of APP cDNA Clones

Figure 11A:
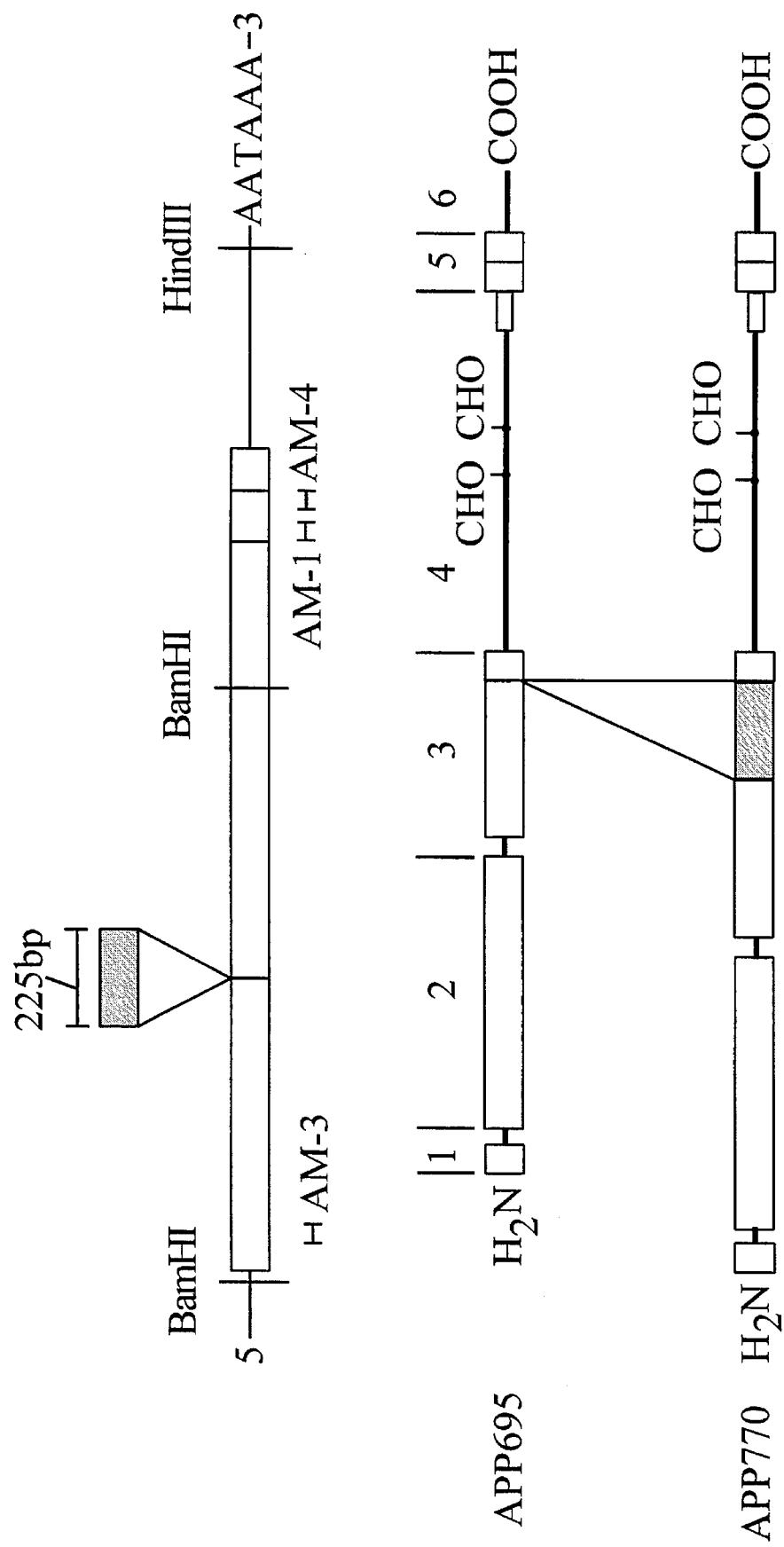

The cDNA clone APP-695 is of the form of cDNA described by Kang, et al., *Nature* 325:733–735 ((1987) (FIG. 9), and represents the most predominant form of Alzheimer's protein in the brain. The cDNA clone APP-751 is of the form described by Ponte, P, *Nature* 331, 525–527 (1988) (FIG. 10). The cDNA clone APP-770 is of the form described by Kitaguchi, et al. *Nature* 331:530–532 (1988) (FIGS. 11a and 11b). This form contains an insert of 225 nucleotides relative to the 695 form. The 225 nucleotide insert encodes for the KI domain as well as the OX-2 domain.

Definition of the APP Genomic Locus

Characterization of phage and cosmid clones of human genomic DNA clones listed in the table below originally established a minimum size of at least 100 kb for the Alzheimer's gene. There are a total of 18 exons in the APP gene (Lemaire et al., *Nucl. Acid Res,* 17:517–522, 1989; Yoshikai et al., 1990) (FIG. 12). These results taken together indicate that the minimum size of the Alzheimer's gene is 175 kb.

| I. Table of Alzheimer's Cosmid and Lambda Clones | | | |
|---|---|---|---|
| Library | Name of Clone | Insert Size (Kb) | Assigned APP Region |
| Cosmid | 1 GPAPP47A | 35 | 25 Kb promoter & 9 Kb intron 1 |
|  | 2 GPAAP36A | 35 | 12 Kb promoter & 22 Kb intron 1 |
|  | 3 GAPP30A | 30–35 | 5' coding region |
|  | 4 GAPP43A | 30–35 | exons 9, 10 and 11 |
| Lambda | 1 GAPP6A | 12 | exon 6 |
|  | 2 GAPP6B | 18 | exons 4 and 5 |
|  | 3 GAPP20A | 20 | exon 6 |
|  | 4 GAPP20B | 17 | exons 4 and 5 |
|  | 5 GAPP28A | 18 | exons 4 and 5 |
|  | 6 GAPP3A | 14 | exon 6 |
|  | 7 GAPP4A | 19 | exon 6 |
|  | 8 GAPP10A | 16 | exons 9, 10 and 11 |
|  | 9 GAPP16A | 21 | exon 6 |

Construction of Transgenes

The clones bearing various portions of the human APP gene sequence shown in FIGS. 1–5 are constructed in an analogous manner. First, the polyA addition signal from SV40 virus as a 253 base pair BclI to BamHI fragment (Reddy et al., *Science* 200:494–502 (1978) is cloned into a modified vector from the pUC series. Next, the cDNA coding sequences (770, 751, or 695) are inserted. Correct orientation and content of the fragments inserted is determined through restriction endonuclease mapping and limited sequencing.

Figure 4A:
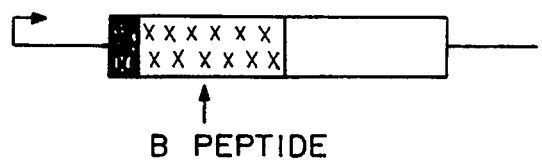
FIG. 4a is a schematic of a coding sequence for the carboxyterminal portion of APP.
Figure 4B:
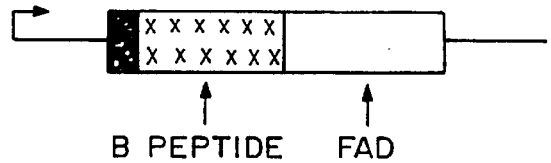
FIG. 4b is a schematic of a coding sequence for the carboxyterminal portion of APP bearing a mutation at position 717.
Figure 5:
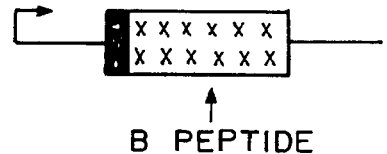
FIG. 5 is a schematic of a coding sequence for the β peptide portion of APP.

The clones bearing various carboxyterminal portions of the human APP gene sequence shown in FIGS. 4 and 5 are constructed through several steps in addition to those indicated above. First, an APP770 cDNA clone is digested with Asp718 which cleaves after position 56 (numbering system of Kang et al., 1987). The resulting 5' extension is filled in using the Klenow enzyme (Maniatis et al., 1989) and ligated to a hexanucleotide of the following sequence: AGATCT, the recognition site for BglII. After cleavage with BglII, which also cuts after position 1769, and religation, the translational reading frame of the protein is preserved. The truncated protein thus encoded contains the leader sequence, followed by approximately 6 amino acids that preceed the β peptide, followed by the β peptide, and the 56 terminal amino acids of APP. The clone in FIG. 5 is created by the introduction through site directed mutagenesis of nucleotide 1913 in the clone of FIG. 4a (numbering system of Kang et al., 1987) to a T thus creating a termination codon directly following the last amino acid codon of the peptide. Each of the APP cDNA sequence clones shown in FIGS. 1–5 contains a single NruI site 2 nucleotides upstream from the initiator methionine codon that is used for attachment of the different promoters used to complete each construct.

Expression clones identical to these but bearing mutations at the amino acid 717 of the full length protein, the site of the FAD mutation, are also constructed. Mutations at amino acid 717 are created by site-directed mutagenesis (Vincent, et al., *Genes & Devel.* 3, 334–347 (1989)) and include mutations of the wild-type val codon to one of the following codons; ile, phe, gly, tyr, leu, ala, pro, trp, met, ser, thr, asn, gln.

Figure 6A:
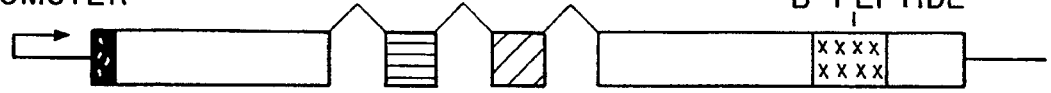
FIG. 6a is a schematic of a combination genomic/cDNA coding sequence allowing alternative splicing of the KI and OX2 exons.
Figure 6B:
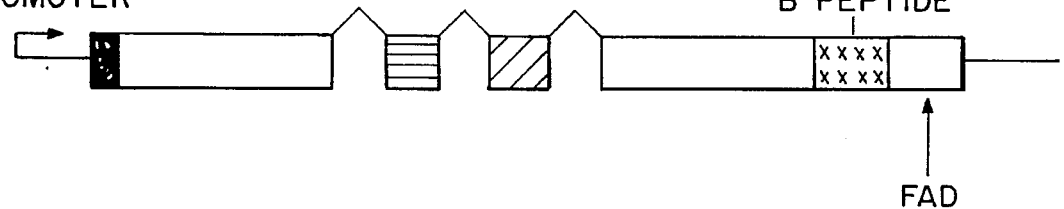
FIG. 6b is a schematic of a combination genomic/cDNA coding sequence bearing a mutation at position 717 and allowing alternative splicing of the KI and OX2 exons.

The preferred method for construction of the combination cDNA/genomic expression clones in FIG. 6 is as follows. The TaqI site at position 860 (numbering system of Kang, et al., 1987) in an APP770 cDNA clone is converted to an XhoI site by site-directed mutagenesis. Cleavage of the resulting plasmid with XhoI cuts at the new XhoI site and a pre-existing site at 930, and releases the KI and OX-2 coding sequence.

The plasmid thus generated serves as the acceptor for the KI and OX-2 alternative splicing cassette. The alternative splicing cassette is created through a series of cloning steps. First, the TaqI site at position 860 (numbering system of Kang, et al., 1987) in the genomic clone containing exon 6 and adjacent downstream intron is converted to an XhoI site by site-directed mutagenesis. Cleavage of the resulting plasmid with XhoI cuts at the new XhoI site and an XhoI site within the adjacent intron. This fragment is cloned into the XhoI site in a plasmid vector. Second, the genomic clone containing exon 9 and adjacent upstream intron is cleaved with XhoI (position 930) and cloned into the XhoI site of a plasmid vector. These two junction exon/intron fragments are released from their respective plasmid backbones by cleavage with XhoI and either BamHI or BglII, and cloned into the XhoI site of a plasmid vector. The resulting XhoI fragment is cleaved with either BamHI or BglII and the genomic 6.6 kb BamHI segment (Kitaguchi et al., 1988) containing the KI and OX-2 coding region identified by Southern blot analysis of BamHI-digested lymphocyte DNA from one normal individual and eight Alzheimer's disease patients with a 212-bp TaqI(nt 862)-AvaI(nt 1,073) fragment of pAPP770 as hybridization probe (FIG. 11b). Genomic DNA clones containing the region of the 225-bp insert were isolated from the human leukocyte DNA library (Clontech, USA) using the 212-bp TaqI-AvaI fragment as probe. In the genomic DNA, the 225-bp sequence was located in a 168-bp exon and a 57-bp exon, separated by an intron of approximately 3 kb, with both exons flanked by intron-exon consensus sequences. The 168-bp exon corresponds to nt 866 to 1,033 of pAPP770, and the 57-bp exon to nt 1,034 to 1,090. Exon I encodes the high conserved region of the protease inhibitor family along with their flanking intron sequences are inserted. After cleavage with XhoI, this DNA segment is inserted into the XhoI site of the modified APP770 cDNA constructed above. These cloning steps generate a combination cDNA/genomic expression clone that allows cells in a transgenic animal to regulate the inclusion of the KI and OX-2 domains by a natural alternative splicing mechanism. An analogous gene bearing a mutation at amino acid 717 is constructed by using the mutated form of APP770 cDNA described above.

Activity of Gene Promoters

Different promoter sequences are used to control expression of APP coding sequences. The ability to regulate expression of the APP gene in transgenic animals is believed to be useful in evaluating the roles of the different APP gene products in AD. The ability to regulate expression of the APP gene in cultured cells is believed to be useful in evaluating expression and processing of the different APP gene products and may provide the basis for cell cultured drug screens.

The metallothionine (MT) promoter is well characterized, has been employed in transgenic animals, and its expression can be regulated through modulation of zinc and glucocorticoid hormone levels (Palmiter et al., *Nature* 300, 611–615 (1982)).

The human APP promoter is also characterized with regard to expression in the CNS. The APP promoter was isolated and cloned in an approximately 4.5 kB EcoRI fragment encompassing the 5'-end of the human APP gene inserted (blunt-end) into the HindIII site of pMTI-2301. The APP genomic fragment was isolated from a human chromosome 21 cell-sorted genomic library obtained from the American Type Culture Collection: ATCC no. LA21NS01, using probe generated from an ApaI-XhoI fragment of APP cDNA. The cloning vector, pMTI-2301, contains a unique cloning site, HindIII, flanked by NotI restriction sites; and was generated by replacing the multiple cloning sites (EcoRI-HindIII restriction fragment) of pWE16 (from Stratagene; the BamHI site was converted to a HindIII site using adapters) (Wirak et al., 1991). It is believed that this promoter is useful for accurately reproducing temporal and spatial expression of human APP sequences in the CNS of transgenic rodents. In addition to the human APP promoter, the APP promoter from mouse and rat is used in conjunction with the various wild-type and mutant APP coding sequences. Although the human APP promoter has been shown to have activity in the appropriate regions of the brain of transgenic mice (Wirak et al., 1991), it is believed that the use of a mouse APP promoter in a transgenic mouse or a rat APP promoter in a transgenic rat will offer an even more precise pattern of expression in the CNS of transgenic animals.

As an alternative for the control of human APP expression in neurons, the rat neuron specific enolase promoter is used. This promoter has been shown to direct expression of coding sequences in neurons (Forss-Petter et al., *Neuron* 5;197–197 (1990)).

Yeast Artificial Chromosomes

The constructs shown in FIG. 7 are constructed as follows. Large segments of human genomic DNA, when cloned into certain vectors, can be propagated as autonomously-replicating units in the yeast cell. Such vector-borne segments are referred to as yeast artificial chromosomes (YAC; Burke et al. *Science* 236,806 (1987)). A human YAC library is commercially available (Clontech, Palo Alto, Calif.) with an average insert size of 250,000 base pairs (range of 180,000 to 500,000 base pairs). A YAC clone of the Alzheimer's gens can be directly isolated by screening the library with the human APP770 cDNA. The inclusion of all of the essential gene regions in the clone can be confirmed by PCR analysis.

The YAC-APP clone, shown in FIG. 7a, is established in embryonic stem (ES) cells by selecting for neomycin resistance encoded by the YAC vector. ES cells bearing the YAC-APP clone are used to produce transgenic mice by established methods described below under "Transgenic Mice" and "Embryonic Stem Cell Methods". The YAC-APP gens bearing a mutation at amino acid 717 (FIG. 7b) is produced through the generation of a YAC library using genomic DNA from a person affected by a mutation at amino acid 717. The clone is identified and established in ES cells as described above.

Genetic Alteration of the Mouse APP Gene

The nucleotide sequence homology between the human and murine Alzheimer's protein genes is approximately 85%. Within the peptide-coding region, there are three amino acid differences between the two sequences. The val residue that is mutated at amino acid 717 is conserved between mouse, rat, and man. Wild-type rodents do not develop Alzheimer's disease nor do they develop deposits or plaques in their CNS analogous to those present in human Alzheimer's patients. Therefore, it is possible that the human but not the rodent form of β peptide is capable of causing disease. Homologous recombination (Capecchi, MR *Science* 244, 1288–1292 (1989)) can be used to convert the mouse Alzheimer's gene in situ to a gene encoding the human β peptide. This recombination is directed to a site downstream from the KI and OX-2 domains, for example, within exon 9, so that the natural alternative splicing mechanisms appropriate to all cells within the transgenic animal can be employed in expressing the final gene product.

Both wild-type (FIG. 8a) and mutant (FIG. 8b) forms of human cDNA are used to produce transgenic models expressing either the wild-type or mutant forms of APP. The recombination vector is constructed from a human APP cDNA (695 or 770 form), either wild-type or mutant at amino acid 717. Cleavage of the recombination vector, for example, at the XhoI site within exon 9, promotes homologous recombination within the directly adjacent sequences (Capecchi, 1989). The endogenous APP gene resulting from this event is normal up to the point of recombination, within exon 9 in this example, and consists of the human cDNA sequence thereafter.

Mutant Forms of APP Proteins

Expression clones identical to these but bearing mutations at the amino acid 717 of the full length protein, the site of FAD mutations, are also constructed. Mutations at amino acid 717 are created by site-directed mutagenesis (Vincent, et al., 1989) and include mutations of the wild-type val codon to one of the following codons; ile, phe, gly, tyr, leu, ala, pro, trp, met, ser, thr, asn, gln. Mutations of val-717 to ile, phe, and gly, have been described (Goate et al., 1991; Murrell, et al., 1991 (FIG. 13); Chartier-harlin et al., 1991). None of these naturally-occurring mutations are charged or bulky amino acids. Therefore it is believed that replacement of val-717 with the other amino acids listed may also promote the FAD syndrome and have properties that are useful for animal AD models.

Preparation of Constructs for Transfections and Microinjections

DNA clones for microinjection are cleaved with appropriate enzymes, such as Sal1, Not1, etc., and the DNA fragments electrophoresed on 1% agarose gels in TBE buffer (Maniatis et al., 1989). The DNA bands are visualized by staining with ethidium bromide, excised, and placed in dialysis bags containing 0.3M sodium acetate, pH 7.0. DNA is electroeluted into the dialysis bags, extracted with phenol-chloroform (1:1), and precipitated by two volumes of ethanol. The DNA is redissolved in 1 ml of low salt buffer (0.2M NaCl, 20 mM Tris™, pH 7.4, and 1 mM EDTA) and purified on an Elutip-D™ column. The column is first primed with 3 ml of high salt buffer (1M NaCl, 20 mM Tris™, pH 7.4, and 1 mM EDTA) followed by washing with 5 ml of low salt buffer. The DNA solutions are passed through the column for three times to bind DNA to the column matrix. After one wash with 3 ml of low salt buffer, the DNA is eluted with 0.4 ml of high salt buffer and precipitated by two volumes of ethanol. DNA concentrations are measured by absorption at 260 nm in a UV spectrophotomer. For microinjection, DNA concentrations are adjusted to 3 µg/ml in 5 mM Tris™, pH 7.4 and 0.1 mM EDTA. Other methods for purification of DNA for microinjection are also described in Hogan, et al., *Manipulating the mouse embryo* (cold Spring Harbor Laboratory, Cold Spring Harbor, N.Y. (1986), in Palmiter, et al.,

*Nature* 300, 611 (1982), in "The Qiagenologist, Application Protocols", 3rd edition, published by Qiagen, Inc., Chatsworth, Calif., and in Maniatis, et al., *Molecular Cloining: a laboratory manual* (Cold Spring Harbor Laboratory, Cold Spring Harbor, N.Y. 1989).

Construction of Transgenie Animals

Animal Sources

Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Swiss Webster female mice are preferred for embryo retrieval and transfer. $B6D2F_1$ males can be used for mating and vasectomized Swiss Webster studs can be used to stimulate pseudopregnancy. Vasectomized mice and rats can be obtained from the supplier.

Microinjection Procedures

The procedures for manipulation of the rodent embryo and for microinjection of DNA are described in detail in Hogan et al. Manipulating the mouse embryo, Cold Spring Harbor Labory, Cold Spring harbor, N.Y. (1986), the teachings of which are incorporated herein.

Transgenic Mice

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10–12 embryos). The pipet tip is inserted into the infundibulum and the embryos transferred. After the transfer, the incision is closed by two sutures.

Transgenic Rats

The procedure for generating transgenic rats is similar to that of mice (Hammer et al., *Cell* 63:1099–112 (1990)). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPBS (Dulbecco's phosphate buffered saline) with 0.5% BSA and the embryos collected. Cumulus cells surronding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10–12 embryos are transferred into each rat oviduct through the infundibulum. The incision is then closed with sutures, and the foster mothers are housed singly.

Embryonic Stem (ES) Cell Methods

Introduction of cDNA into ES Cells

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987), the teachings of which are incorporated herein. Selection of the desired clone of transgene-containing ES cells is accomplished through one of several means. In cases involving random gene integration, an APP clone is co-precipitated with a gene encoding neomycin resistance. Transfection is carried out by one of several methods described in detail in Lovell-Badge, in *Teratocarcinomas and embryonic stem cells, a practical approach*, ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, $0.5 \times 10^6$ ES cells are plated into tissue culture dishes and transfected with a mixture of the linearized APP clone and 1 mg of pSV2neo DNA (Southern and Berg, *J. Mol Appl Gen.* 1:327–341 (1982)) precipitated in the presence of 50 mg lipofectin in a final volume of 100 μl. The cells are fed with selection medium containing 10% fetal bovine serum in DMEM supplemented with G418 (between 200 and 500 μg/ml). Colonies of cells resistant to G418 are isolated using cloning rings and expanded. DNA is extracted from drug resistant clones and Southern blotting experiments using an APP770 cDNA probe are used to identify those clones carrying the APP sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989). DNA introduction by electroporation is less efficient and requires a selection step. Methods for positive selection of the recombination event (i.e., neo resistance) and dual positive-negative selection (i.e., neo resistance and gancyclovir resistance) and the subsequent identification of the desired clones by PCR have been described by Joyner et al., *Nature* 338, 153–156 (1989) and Capecchi, (1989), the teachings of which are incorporated herein.

Embryo Recovery and ES Cell Injection

Naturally cycling or superovulated female mice mated with males are used to harvest embryos for the implantation of ES cells. It is desirable to use the C57B strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10–20 ES cells are injected into blastocysts using a glass microneedle with an internal diameter of approximately 20 μm.

Transfer of Embryos to Pseudopregnant Females

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 guage needle through which the blastocysts are transferred. After the transfer, the ovary and uterus are pushed back into the body and the incision is closed by two sutures. This procedure is repeated on the opposite side if additional transfers are to be made.

Identification of Transgenic Mice and Rats

Tail samples (1–2 cm) are removed from three week old animals. DNA is prepared and analyzed by both Southern blot and PCR to detect transgenic founder ($F_0$) animals and their progeny ($F_1$ and $F_2$).

Pathological Studies

The various $F_0$, $F_1$, and $F_2$ animals that carry the microinjected transgene are sacrificed by $CO_2$ asphyxiation and analyzed by immunohistology for neuritic plaques and neurofibrillary tangles (NFTs) in the brain. Brains of mice and rats from each transgenic line are fixed in 4% paraformladehyde and sectioned on a cryostat. Sections are stained with antibodies reactive with the APP and/or the β peptide. Secondary antibodies conjugated with fluorescein, rhodamine, horse radish peroxidase, or alkaline phosphatase are used to detect the primary antibody. These experiments permit identification of amyloid plaques and the regionalization of these plaques to specific areas of the brain. Plaques ranging in size from 9 to 50 μm characteristically occur in the brains of AD patients in the cerebral cortex, but also may be observed in deeper grey matter including the amygdaloid nucleus, corpus striatum and diencephalon. Sections are also stained with other antibodies diagnostic of Alzheimer's plaques, recognizing antigens such as Alz-50, tau, A2B5, neurofilaments, neuron-specific enolase, and others that are characteristic of Alzheimerts plaques (Wolozin, et al., *Science* 232, 648 (1986); Hardy and Allsop, *Trends in Pharm. Sci.* 12, 383–388 (1991); Selkoe, *Ann. Rev. Neurosci.* 12, 463–490 (1989); Arai et al., *Proc. Natl. Acad. Sci. USA* 87, 2249–2253 (1990); Majocha et al., *Amer. Associ. Neuropathology* Abs; 99,22 (1988); Masters et al., *Proc Nat Acad Sci* 82,4245–4249; Majocha et al., *Can J Biochem Cell Biol* 63;577–584 (1985)). Staining with thioflavins and congo red is also carried out to analyze co-localization of β peptide deposits within neuritic plaques and NFTs.

Analysis of APP and β Peptide Expression mRNA: mRNA is isolated by the acid guanidinium thiocyanatephenol:chloroform extraction method (Chomczynski and Sacchi, *Anal Biochem* 162,156–159 (1987)) from cell lines and tissues of transgenic animals to determine expression levels by Northern blots.

Protein: APP and β peptide are detected by using polyclonal and monoclonal antibodies that are specific to the extracytoplasmic domain, β peptide region, and C-terminus.

Western Blot Analysis: Protein fractions are isolated from tissue homogenenates and cell lysates and subjected to Western blot analysis as described by Harlow et al., *Antibodies: A laboratory manual*, (Cold Spring Harbor, N.Y., 1988); Brown et al., *J. Neurochem* 40;299–308 (1983); and Tate-Ostroff et al., *Proc Natl Acad Sci* 86;745–749 (1989)). Only a brief description is given below.

The protein fractions are denatured in Laemmli sample buffer and electrophoresed on SDS-Polyacrylamide gels. The proteins are be then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of APP proteins.

Pathological and Behavioral Studies

Pathological Studies

Immunohistology and thioflavin S staining are conducted as described elsewhere herein.

In situ Hybridizations: Radioactive or enzymatically labeled probes are used to detect mRNA in situ. The probes are degraded approximately to 100 nucleotides in length for better penetration of cells. The procedure of Chou et al. *J Psychiatr Res* 24,27–50 (1990) for fixed and paraffin embedded samples is briefly described below although similar procedures can be employed with samples sectioned as frozen material. Paraffin slides for in situ hybridization are dewaxed in xylene and rehydrated in a graded series of ethanols and finally rinsed in phosphate buffered saline (PBS). The sections are postfixed in fresh 4% paraformaldehyde. The slides are washed with PBS twice for 5 minutes to remove paraformaldehyde. Then the sections are permeabilized by treatment with a 20 μg/ml proteinase K solution. The sections are refixed in 4% paraformaldehyde, and basic molecules that could give rise to background probe binding are acetylated in a 0.1M triethanolamine, 0.3M acetic anhydride solution for 10 minutes. The slides are washed in PBS, then dehydrated in a graded series of ethanols and air dried. Sections are hybridized with antisense probe, using sense probe as a control. After appropriate washing, bound radioactive probes are detected by autoradiography or enzymatically labeled probes are detected through reaction with the appropriate chromogenic substrates.

Behavioral Studies of Transgenic Mice and Rats

Behavioral tests designed to assess learning and memory deficits are employed. An example of such as test is the Morris Water maze (Morris, *Learn Motivat* 12;239–260

(1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues.

The procedures applied to test transgenic mice is similar for transgenic rats.

Screening of Compounds for treatment of Alzheimer's Disease

The transgenic animals and animal cells are used to screen compounds for a potential effect in the treatment of Alzheimer's disease using standard methodology. The compound is administered to the animals or introduced into the culture media over a period of time and in various dosages, then the animals or animal cells examined for alterations in APP expression, histopathology, and/or behavior using the procedures described above.

EXAMPLE 1

Expression of pMTAPP-1 in NIH3T3 and PC12 Cells

The clone, pMTAPP-1 is an example of the expression vector shown in FIG. 1a where the promoter used is the metallothionine promoter. Stable cell lines were derived by transfecting NIH3T3 and PC12 cell lines (ATCC #CCL92 and CRL1721). $0.5\times10^6$ of NIH3T3 or PC12 cells were plated into 100 mm dishes and transfected with a mixture of 5 mg of the Sal1 fragment and 1 mg of pSV2neo DNA (46) precipitated in the presence of 50 mg lipofectin (Gibco, BRL) in a final volume of 100 μl. Polylysine-coated plates were used for PC12 cells, which normally do not adhere well to tissue culture dishes. The cells were fed with selection medium containing 10% fetal bovine serum in DMEM or RPMI and supplemented with G418. Five hundred mg/ml (biological weight) and 250 mg/ml of G418 were used to select colonies form NIH3T3 and PC12 cells, respectively. Fifteen days after transfection, colonies of cells resistant to G418 were isolated by cloning rings and expanded in T flasks. The presence of APP cDNA in the cells was detected by PCR using the procedure of Mullis and Faloona, *Methods Enzymol* 155:335–350 (1987), the teachings of which are incorporated herein.

Expression of APP in 25 colonies from each cell line was analyzed by immunostaining (Majocha et al., 1988). Cells were grown to subconfluence and fixed in a solution containing 4% paraformaldehyde, 0.12M NaCl, and 20 mm $Na_3PO_4$, pH 7.0. They were incubated overnight with a primary monoclonal antibody against a synthetic β peptide sequence (Masters et al., 1985) provided by Dr. Ronald Majocha, Massachusetts General Hospital, Boston, Mass., followed by a generalized anti-mouse antibody conjugated to biotin (Jackson ImmunoResearch Labs, Pa.). Immunostaining was then performed by adding avidin-horseradish peroxidase (HRP) (Vector Labs, Burlingame, Calif.) and diaminobenzidine as the chromogen (Majocha et al., 1985). The results indicated that the pMTAPP-1 vector was expressing APP in both NIH3T3 and PC12 cells.

EXAMPLE 2

Expression of pEAPP-1 in PC12 Cells pEAPP-1 is an example of the 25 kb human APP gene promoter linked to and controlling expression of a human APP770 cDNA like the construct in FIG. 1A. DNA from this construct was transfected into PC12 cells as described above. Certain clones of pEAPP-1 transfected cells exhibited a differentiation phenotype morphologically similar to that exhibited by PC12 cells treated with nerve growth factor (NGF). PC12 cells normally are fairly round and flat cells. Those transfected with pEAPP-1 have cytoplasmic extensions resembling neurites. PC12 cells treated with NGF extend very long neuritic extensions. Thirteen PC12 cell clones transfected with pEAPP-1 were selected and propagated. Eight of these cell clones exhibited the spontaneous differentiation phenotype with clones 1-8, 1-1, and 1-4 exhibiting the strongest phenotypes. Staining of pEAPP-1 tranfected PC12 cells with antibody against the β peptide as described above indicated that those cells exhibiting the differentiation were also expressing APP. Because PC12 cells transfected with the pMTAPP1 clone did not exhibit this phenotype even though the APP770 cDNA is expressed, these results suggest that expression of APP770 from the human promoter has novel properties regarding the physiology of the cell.

EXAMPLE 3

Expression of pMTA4 in PC12 Cells pMTA4 is an example of the type of construct shown in FIG. 4A where the promoter used is the metallothionine promoter. The protein encoded by this construct differs slightly from that depicted in FIG. 4. An APP770 cDNA clone was digested with Asp718 which cleaves after position 56 (number system of Kang, et al., 1987). The resulting 5' extension was filled in using the Klenow enzyme (Maniatis). The same DNA preparation was also cleaved with EcoRI which also cuts after position 1795 and the resulting 5' extension was filled in using the Klenow enzyme (Maniatis). Self-ligation of this molecule results in an expression clone in which the truncated protein thus encoded contains the leader sequence, followed by a shortened version of the β peptide starting with the sequence phe-arg-val-gly-ser-of the β peptide followed by the 56 terminal amino acids of APP. DNA from this construct was transfected into PC12 cells as described above.

EXAMPLE 4

Generation of Transgenic Mice Expressing APP Under the Control of the MT-1 Promoter Transgenic mice were made by microinjecting pMTAPP1 vector DNA into pronuclear embryos. pMTAPP1 is an example of the type of construct shown in FIG. 1a which is operably linked to the metallothionine promoter. The procedures for microinjection into mouse embryos are described in "Manipulating the mouse embryo" by B. Hogan et al. (1986). Only a brief description of the procedures is described below.

Mice were obtained from Taconic Laboratories (German Town, N.Y.). Swiss Webster female mice were used for embryo retrieval and implantation. $B6D2F_1$ males were used for mating and vasectomized Swiss webster studs were used to simulate pseudopregnancy.

Embryo Recovery: Female mice, 4 to 8 weeks of age, were induced to superovulate with 5 IU of pregnant mare's serum gonadotropin (PMSG; Sigma) followed 48 hours later by 5 IU of human chorionic gonadotropin (hCG; Sigma). Females were placed with males immediately after hCG injection. Embryos were recovered from excised oviducts of mated females 21 hours after hCG in Dulbecco's phosphate buffered saline with 0.5% bovine serum albumin (BSA; Sigma). Surrounding cumulus cells were removed with hyaluronidase (1 mg/ml). Pronuclear embryos were then washed and placed in Earle's balanced salt solution containing 0.4% BSA (EBSS) in a 37.5° C. incubator with a humidified atmosphere at 7% $CO_2$, 5% $O_2$, and 88% $N_2$ until the time of injection.

Microinjection: Elutip-D™ purified Sal1 DNA was dissolved in 5 mM Tris (pH7.4) and 0.1 mM EDTA at 3 μg/ml concentration for microinjection. Microneedles and holding pipettes were pulled from Fisher coagulation tubes (Fisher) on a DKI model 720 pipette puller. Holding pipettes were then broken at approximately 70 μm (O.D.) and fire polished to an I.D. of about 30 μm on a Narishige microforge (model MF-83). Pipettes were mounted on Narishige micromanipulators which were attached to a Nikon Diaphot microscope. The air-filled injection pipette was filled with DNA solution through the tip after breaking the tip against the holding pipette. Embryos, in groups of 30 to 40, were placed in 100 μl drops of EBBS under paraffin oil for micromanipulation. An embryo was oriented and held with the holding pipette. The injection pipette was then inserted into the male pronucleus (usually the larger one). If the pipette did not break through the membrane immediately the stage was tapped to assist in penetration. The nucleus was then injected and the injection was monitored by swelling of the nucleus. Following injection, the group of embryos was placed in EBSS until transfer to recipient females.

Transfer: Randomly cycling adult female mice were paired with vasectomized Swiss Webster males. Recipient females were mated at the same time as donor females. At the time of transfer, the females were anesthetized with avertin. The oviducts were exposed by a single midline dorsal incision. An incision was then made through the body wall directly over the oviduct. The ovarian bursa was then torn with watch makers forceps. Embryos to be transferred were placed in DPBS and in the tip of a transfer pipet (about 10–12 embryos). The pipet tip was inserted into the infundibulum and embryos were transferred. After the transfer, the incision was closed by two sutures.

Analysis Of Mice For Transgene Integration: At three weeks of age tail samples about 1 cm long were excised for DNA analysis. The tail samples were digested by incubating with shaking overnight at 55° C. in the presence of 0.7 ml 5 mM Tris, pH 8.0, 100 mM EDTA, 0.5% SDS and 350 μg of proteinase K. The digested material was extracted once with an equal volume of phenol and once with an equal volume of phenol:chloroform (1:1 mixture). The supernatants were mixed with 70 μl 3M sodium acetate (pH 6.0) and the DNAs were precipitated by adding equal volume of 100% ethanol. The DNAs were spun down in a microfuge, washed once with 70% ethanol, dried and dissolved in 100 μl TE buffer (10 mM tris pH 8.0 and 1 mM EDTA).

10–20 μl of DNAs were restricted with BamH1, electrophoresed on 1% agarose gels, blotted onto nitrocellulose paper, and hybridized with $^{32}P$-labeled APP cDNA fragment. Transgenic animals were identified by autoradiography of the hybridized nitrocellulose filters. The DNAs were also analyzed by PCR carried out by synthetic primers to generate an 800 bp fragment.

A total of 671 pronuclear embryos were microinjected out of which 73 live and 6 dead pups were born. DNA analysis identified 9 transgenic mice (5 females and 4 males) which were bred to generate $F_1$ and $F_2$ transgenics. These animals can be analyzed for expression of mRNA and protein of APP in different tissues and for analysis of behavioral and pathological abnormalities as described above.

Modifications and variations of the making and testing of transgenic animal models for testing of Alzheimer's disease will beobvious to those skilled in the art from the foregoing detailed description. Such modifications and variations are intended to come within the scope of the following claims.

---

We claim:

1. A nucleic acid construct comprising a mammalian promoter operatively linked to a cDNA-genomic DNA hybrid sequence, wherein said hybrid sequence contains a cDNA sequence encoding APP770 or a cDNA sequence encoding APP770 with a naturally occurring mutation, wherein a genomic APP DNA sequence consisting of exon 6 and an amount of the adjacent downstream intron sufficient for splicing, the KI and OX-2 coding region and an amount of each of their upstream and downstream introns sufficient for splicing, and exon 9 and an amount of the adjacent upstream intron sufficient for splicing is substituted into the corresponding region of the cDNA sequence encoding APP770, or the cDNA encoding APP770 with a naturally occurring mutation, and wherein the construct is transcribed and differentially spliced in mammalian cells to form mRNA molecules which encode and are translated into APP695, APP751 and APP770.

2. The construct of claim 1 wherein the promoter is selected from the group consisting of the human APP promoter, metallothionine promoter, rat neuron specific enolase promoter and human platelet derived growth factor B chain promoter.

3. The construct of claim 1 wherein the promoter regulates expression of the hybrid sequence in a rodent.

\* \* \* \* \*

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 3353 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 147..2231

( x i ) SEQUENCE DESCRIPTION: SEQ ID NO:1:

```
AGTTTCCTCG   GCAGCGGTAG   GCGAGAGCAC   GCGGAGGAGC   GTGCGCGGGG   CCCCGGGAGA        60

CGGCGGCGGT   GGCGGCGCGG   GCAGAGCAAG   GACGCGGCGG   ATCCCACTCG   CACAGCAGCG       120

CACTCGGTGC   CCCGCGCAGG   GTCGCG ATG   CTG   CCC   GGT   TTG   GCA   CTG   CTC   CTG       173
```

|  |  |  |  |  |  |  |  | Met | Leu | Pro | Gly | Leu | Ala | Leu | Leu | Leu |  |
|---|---|---|---|---|---|---|---|---|---|---|---|---|---|---|---|---|---|
|  |  |  |  |  |  |  |  | 1 |  |  |  | 5 |  |  |  |  |  |

| CTG | GCC | GCC | TGG | ACG | GCT | CGG | GCG | CTG | GAG | GTA | CCC | ACT | GAT | GGT | AAT | 221 |
|-----|-----|-----|-----|-----|-----|-----|-----|-----|-----|-----|-----|-----|-----|-----|-----|-----|
| Leu | Ala | Ala | Trp | Thr | Ala | Arg | Ala | Leu | Glu | Val | Pro | Thr | Asp | Gly | Asn |     |
| 10  |     |     |     |     | 15  |     |     |     | 20  |     |     |     |     |     | 25  |     |

| GCT | GGC | CTG | CTG | GCT | GAA | CCC | CAG | ATT | GCC | ATG | TTC | TGT | GGC | AGA | CTG | 269 |
|-----|-----|-----|-----|-----|-----|-----|-----|-----|-----|-----|-----|-----|-----|-----|-----|-----|
| Ala | Gly | Leu | Leu | Ala | Glu | Pro | Gln | Ile | Ala | Met | Phe | Cys | Gly | Arg | Leu |     |
|     |     |     |     | 30  |     |     |     |     | 35  |     |     |     |     | 40  |     |     |

| AAC | ATG | CAC | ATG | AAT | GTC | CAG | AAT | GGG | AAG | TGG | GAT | TCA | GAT | CCA | TCA | 317 |
|-----|-----|-----|-----|-----|-----|-----|-----|-----|-----|-----|-----|-----|-----|-----|-----|-----|
| Asn | Met | His | Met | Asn | Val | Gln | Asn | Gly | Lys | Trp | Asp | Ser | Asp | Pro | Ser |     |
|     |     |     | 45  |     |     |     |     | 50  |     |     |     |     | 55  |     |     |     |

| GGG | ACC | AAA | ACC | TGC | ATT | GAT | ACC | AAG | GAA | GGC | ATC | CTG | CAG | TAT | TGC | 365 |
|-----|-----|-----|-----|-----|-----|-----|-----|-----|-----|-----|-----|-----|-----|-----|-----|-----|
| Gly | Thr | Lys | Thr | Cys | Ile | Asp | Thr | Lys | Glu | Gly | Ile | Leu | Gln | Tyr | Cys |     |
|     |     | 60  |     |     |     |     | 65  |     |     |     |     | 70  |     |     |     |     |

| CAA | GAA | GTC | TAC | CCT | GAA | CTG | CAG | ATC | ACC | AAT | GTG | GTA | GAA | GCC | AAC | 413 |
|-----|-----|-----|-----|-----|-----|-----|-----|-----|-----|-----|-----|-----|-----|-----|-----|-----|
| Gln | Glu | Val | Tyr | Pro | Glu | Leu | Gln | Ile | Thr | Asn | Val | Val | Glu | Ala | Asn |     |
|     |     | 75  |     |     |     |     | 80  |     |     |     |     | 85  |     |     |     |     |

| CAA | CCA | GTG | ACC | ATC | CAG | AAC | TGG | TGC | AAG | CGG | GGC | CGC | AAG | CAG | TGC | 461 |
|-----|-----|-----|-----|-----|-----|-----|-----|-----|-----|-----|-----|-----|-----|-----|-----|-----|
| Gln | Pro | Val | Thr | Ile | Gln | Asn | Trp | Cys | Lys | Arg | Gly | Arg | Lys | Gln | Cys |     |
| 90  |     |     |     |     | 95  |     |     |     |     | 100 |     |     |     |     | 105 |     |

| AAG | ACC | CAT | CCC | CAC | TTT | GTG | ATT | CCC | TAC | CGC | TGC | TTA | GTT | GGT | GAG | 509 |
|-----|-----|-----|-----|-----|-----|-----|-----|-----|-----|-----|-----|-----|-----|-----|-----|-----|
| Lys | Thr | His | Pro | His | Phe | Val | Ile | Pro | Tyr | Arg | Cys | Leu | Val | Gly | Glu |     |
|     |     |     |     | 110 |     |     |     |     | 115 |     |     |     |     | 120 |     |     |

| TTT | GTA | AGT | GAT | GCC | CTT | CTC | GTT | CCT | GAC | AAG | TGC | AAA | TTC | TTA | CAC | 557 |
|-----|-----|-----|-----|-----|-----|-----|-----|-----|-----|-----|-----|-----|-----|-----|-----|-----|
| Phe | Val | Ser | Asp | Ala | Leu | Leu | Val | Pro | Asp | Lys | Cys | Lys | Phe | Leu | His |     |
|     |     |     | 125 |     |     |     |     | 130 |     |     |     |     | 135 |     |     |     |

| CAG | GAG | AGG | ATG | GAT | GTT | TGC | GAA | ACT | CAT | CTT | CAC | TGG | CAC | ACC | GTC | 605 |
|-----|-----|-----|-----|-----|-----|-----|-----|-----|-----|-----|-----|-----|-----|-----|-----|-----|
| Gln | Glu | Arg | Met | Asp | Val | Cys | Glu | Thr | His | Leu | His | Trp | His | Thr | Val |     |
|     |     | 140 |     |     |     |     | 145 |     |     |     |     | 150 |     |     |     |     |

| GCC | AAA | GAG | ACA | TGC | AGT | GAG | AAG | AGT | ACC | AAC | TTG | CAT | GAC | TAC | GGC | 653 |
|-----|-----|-----|-----|-----|-----|-----|-----|-----|-----|-----|-----|-----|-----|-----|-----|-----|
| Ala | Lys | Glu | Thr | Cys | Ser | Glu | Lys | Ser | Thr | Asn | Leu | His | Asp | Tyr | Gly |     |
|     | 155 |     |     |     |     | 160 |     |     |     |     | 165 |     |     |     |     |     |

| ATG | TTG | CTG | CCC | TGC | GGA | ATT | GAC | AAG | TTC | CGA | GGG | GTA | GAG | TTT | GTG | 701 |
|-----|-----|-----|-----|-----|-----|-----|-----|-----|-----|-----|-----|-----|-----|-----|-----|-----|
| Met | Leu | Leu | Pro | Cys | Gly | Ile | Asp | Lys | Phe | Arg | Gly | Val | Glu | Phe | Val |     |
| 170 |     |     |     |     | 175 |     |     |     |     | 180 |     |     |     |     | 185 |     |

| TGT | TGC | CCA | CTG | GCT | GAA | GAA | AGT | GAC | AAT | GTG | GAT | TCT | GCT | GAT | GCG | 749 |
|-----|-----|-----|-----|-----|-----|-----|-----|-----|-----|-----|-----|-----|-----|-----|-----|-----|
| Cys | Cys | Pro | Leu | Ala | Glu | Glu | Ser | Asp | Asn | Val | Asp | Ser | Ala | Asp | Ala |     |
|     |     |     |     | 190 |     |     |     |     | 195 |     |     |     |     | 200 |     |     |

| GAG | GAG | GAT | GAC | TCG | GAT | GTC | TGG | TGG | GGC | GGA | GCA | GAC | ACA | GAC | TAT | 797 |
|-----|-----|-----|-----|-----|-----|-----|-----|-----|-----|-----|-----|-----|-----|-----|-----|-----|
| Glu | Glu | Asp | Asp | Ser | Asp | Val | Trp | Trp | Gly | Gly | Ala | Asp | Thr | Asp | Tyr |     |
|     |     |     | 205 |     |     |     |     | 210 |     |     |     |     | 215 |     |     |     |

| GCA | GAT | GGG | AGT | GAA | GAC | AAA | GTA | GTA | GAA | GTA | GCA | GAG | GAG | GAA | GAA | 845 |
|-----|-----|-----|-----|-----|-----|-----|-----|-----|-----|-----|-----|-----|-----|-----|-----|-----|
| Ala | Asp | Gly | Ser | Glu | Asp | Lys | Val | Val | Glu | Val | Ala | Glu | Glu | Glu | Glu |     |
|     |     | 220 |     |     |     |     | 225 |     |     |     |     | 230 |     |     |     |     |

| GTG | GCT | GAG | GTG | GAA | GAA | GAA | GAA | GCC | GAT | GAT | GAC | GAG | GAC | GAT | GAG | 893 |
|-----|-----|-----|-----|-----|-----|-----|-----|-----|-----|-----|-----|-----|-----|-----|-----|-----|
| Val | Ala | Glu | Val | Glu | Glu | Glu | Glu | Ala | Asp | Asp | Asp | Glu | Asp | Asp | Glu |     |
|     | 235 |     |     |     |     | 240 |     |     |     |     | 245 |     |     |     |     |     |

| GAT | GGT | GAT | GAG | GTA | GAG | GAA | GAG | GCT | GAG | GAA | CCC | TAC | GAA | GAA | GCC | 941 |
|-----|-----|-----|-----|-----|-----|-----|-----|-----|-----|-----|-----|-----|-----|-----|-----|-----|
| Asp | Gly | Asp | Glu | Val | Glu | Glu | Glu | Ala | Glu | Glu | Pro | Tyr | Glu | Glu | Ala |     |
| 250 |     |     |     | 255 |     |     |     |     | 260 |     |     |     |     |     | 265 |     |

| ACA | GAG | AGA | ACC | ACC | AGC | ATT | GCC | ACC | ACC | ACC | ACC | ACC | ACA | GAG |  | 989 |
|-----|-----|-----|-----|-----|-----|-----|-----|-----|-----|-----|-----|-----|-----|-----|--|-----|
| Thr | Glu | Arg | Thr | Thr | Ser | Ile | Ala | Thr | Thr | Thr | Thr | Thr | Thr | Glu |  |     |
|     |     |     |     | 270 |     |     |     |     | 275 |     |     |     |     | 280 |  |     |

| TCT | GTG | GAA | GAG | GTG | GTT | CGA | GTT | CCT | ACA | ACA | GCA | GCC | AGT | ACC | CCT | 1037 |
|-----|-----|-----|-----|-----|-----|-----|-----|-----|-----|-----|-----|-----|-----|-----|-----|------|
| Ser | Val | Glu | Glu | Val | Val | Arg | Val | Pro | Thr | Thr | Ala | Ala | Ser | Thr | Pro |      |
|     |     |     | 285 |     |     |     |     | 290 |     |     |     |     | 295 |     |     |      |

| GAT | GCC | GTT | GAC | AAG | TAT | CTC | GAG | ACA | CCT | GGG | GAT | GAG | AAT | GAA | CAT | 1085 |
|-----|-----|-----|-----|-----|-----|-----|-----|-----|-----|-----|-----|-----|-----|-----|-----|------|
| Asp | Ala | Val | Asp | Lys | Tyr | Leu | Glu | Thr | Pro | Gly | Asp | Glu | Asn | Glu | His |      |
|     |     | 300 |     |     |     |     | 305 |     |     |     |     | 310 |     |     |     |      |

| GCC | CAT | TTC | CAG | AAA | GCC | AAA | GAG | AGG | CTT | GAG | GCC | AAG | CAC | CGA | GAG | 1133 |

|     |     |     |     |     |     |     |     |     |     |     |     |     |     |     |     |
|---|---|---|---|---|---|---|---|---|---|---|---|---|---|---|---|
| Ala | His | Phe | Gln | Lys | Ala | Lys | Glu | Arg | Leu | Glu | Ala | Lys | His | Arg | Glu |
| 315 |     |     |     |     | 320 |     |     |     |     | 325 |     |     |     |     |     |

| AGA | ATG | TCC | CAG | GTC | ATG | AGA | GAA | TGG | GAA | GAG | GCA | GAA | CGT | CAA | GCA | 1181 |
|---|---|---|---|---|---|---|---|---|---|---|---|---|---|---|---|---|
| Arg | Met | Ser | Gln | Val | Met | Arg | Glu | Trp | Glu | Glu | Ala | Glu | Arg | Gln | Ala |  |
| 330 |  |  |  |  | 335 |  |  |  |  | 340 |  |  |  |  | 345 |  |

| AAG | AAC | TTG | CCT | AAA | GCT | GAT | AAG | AAG | GCA | GTT | ATC | CAG | CAT | TTC | CAG | 1229 |
|---|---|---|---|---|---|---|---|---|---|---|---|---|---|---|---|---|
| Lys | Asn | Leu | Pro | Lys | Ala | Asp | Lys | Lys | Ala | Val | Ile | Gln | His | Phe | Gln |  |
|  |  |  |  | 350 |  |  |  |  | 355 |  |  |  |  | 360 |  |  |

| GAG | AAA | GTG | GAA | TCT | TTG | GAA | CAG | GAA | GCA | GCC | AAC | GAG | AGA | CAG | CAG | 1277 |
|---|---|---|---|---|---|---|---|---|---|---|---|---|---|---|---|---|
| Glu | Lys | Val | Glu | Ser | Leu | Glu | Gln | Glu | Ala | Ala | Asn | Glu | Arg | Gln | Gln |  |
|  |  |  | 365 |  |  |  |  | 370 |  |  |  |  | 375 |  |  |  |

| CTG | GTG | GAG | ACA | CAC | ATG | GCC | AGA | GTG | GAA | GCC | ATG | CTC | AAT | GAC | CGC | 1325 |
|---|---|---|---|---|---|---|---|---|---|---|---|---|---|---|---|---|
| Leu | Val | Glu | Thr | His | Met | Ala | Arg | Val | Glu | Ala | Met | Leu | Asn | Asp | Arg |  |
|  |  | 380 |  |  |  |  | 385 |  |  |  |  | 390 |  |  |  |  |

| CGC | CGC | CTG | GCC | CTG | GAG | AAC | TAC | ATC | ACC | GCT | CTG | CAG | GCT | GTT | CCT | 1373 |
|---|---|---|---|---|---|---|---|---|---|---|---|---|---|---|---|---|
| Arg | Arg | Leu | Ala | Leu | Glu | Asn | Tyr | Ile | Thr | Ala | Leu | Gln | Ala | Val | Pro |  |
|  | 395 |  |  |  |  | 400 |  |  |  |  | 405 |  |  |  |  |  |

| CCT | CGG | CCT | CGT | CAC | GTG | TTC | AAT | ATG | CTA | AAG | AAG | TAT | GTC | CGC | GCA | 1421 |
|---|---|---|---|---|---|---|---|---|---|---|---|---|---|---|---|---|
| Pro | Arg | Pro | Arg | His | Val | Phe | Asn | Met | Leu | Lys | Lys | Tyr | Val | Arg | Ala |  |
| 410 |  |  |  |  | 415 |  |  |  |  | 420 |  |  |  |  | 425 |  |

| GAA | CAG | AAG | GAC | AGA | CAG | CAC | ACC | CTA | AAG | CAT | TTC | GAG | CAT | GTG | CGC | 1469 |
|---|---|---|---|---|---|---|---|---|---|---|---|---|---|---|---|---|
| Glu | Gln | Lys | Asp | Arg | Gln | His | Thr | Leu | Lys | His | Phe | Glu | His | Val | Arg |  |
|  |  |  |  | 430 |  |  |  |  | 435 |  |  |  |  | 440 |  |  |

| ATG | GTG | GAT | CCC | AAG | AAA | GCC | GCT | CAG | ATC | CGG | TCC | CAG | GTT | ATG | ACA | 1517 |
|---|---|---|---|---|---|---|---|---|---|---|---|---|---|---|---|---|
| Met | Val | Asp | Pro | Lys | Lys | Ala | Ala | Gln | Ile | Arg | Ser | Gln | Val | Met | Thr |  |
|  |  |  | 445 |  |  |  |  | 450 |  |  |  |  | 455 |  |  |  |

| CAC | CTC | CGT | GTG | ATT | TAT | GAG | CGC | ATG | AAT | CAG | TCT | CTC | TCC | CTG | CTC | 1565 |
|---|---|---|---|---|---|---|---|---|---|---|---|---|---|---|---|---|
| His | Leu | Arg | Val | Ile | Tyr | Glu | Arg | Met | Asn | Gln | Ser | Leu | Ser | Leu | Leu |  |
|  |  | 460 |  |  |  |  | 465 |  |  |  |  | 470 |  |  |  |  |

| TAC | AAC | GTG | CCT | GCA | GTG | GCC | GAG | GAG | ATT | CAG | GAT | GAA | GTT | GAT | GAG | 1613 |
|---|---|---|---|---|---|---|---|---|---|---|---|---|---|---|---|---|
| Tyr | Asn | Val | Pro | Ala | Val | Ala | Glu | Glu | Ile | Gln | Asp | Glu | Val | Asp | Glu |  |
| 475 |  |  |  |  | 480 |  |  |  |  | 485 |  |  |  |  |  |  |

| CTG | CTT | CAG | AAA | GAG | CAA | AAC | TAT | TCA | GAT | GAC | GTC | TTG | GCC | AAC | ATG | 1661 |
|---|---|---|---|---|---|---|---|---|---|---|---|---|---|---|---|---|
| Leu | Leu | Gln | Lys | Glu | Gln | Asn | Tyr | Ser | Asp | Asp | Val | Leu | Ala | Asn | Met |  |
| 490 |  |  |  |  | 495 |  |  |  |  | 500 |  |  |  |  | 505 |  |

| ATT | AGT | GAA | CCA | AGG | ATC | AGT | TAC | GGA | AAC | GAT | GCT | CTC | ATG | CCA | TCT | 1709 |
|---|---|---|---|---|---|---|---|---|---|---|---|---|---|---|---|---|
| Ile | Ser | Glu | Pro | Arg | Ile | Ser | Tyr | Gly | Asn | Asp | Ala | Leu | Met | Pro | Ser |  |
|  |  |  |  | 510 |  |  |  |  | 515 |  |  |  |  | 520 |  |  |

| TTG | ACC | GAA | ACG | AAA | ACC | ACC | GTG | GAG | CTC | CTT | CCC | GTG | AAT | GGA | GAG | 1757 |
|---|---|---|---|---|---|---|---|---|---|---|---|---|---|---|---|---|
| Leu | Thr | Glu | Thr | Lys | Thr | Thr | Val | Glu | Leu | Leu | Pro | Val | Asn | Gly | Glu |  |
|  |  |  |  | 525 |  |  |  |  | 530 |  |  |  |  | 535 |  |  |

| TTC | AGC | CTG | GAC | GAT | CTC | CAG | CCG | TGG | CAT | TCT | TTT | GGG | GCT | GAC | TCT | 1805 |
|---|---|---|---|---|---|---|---|---|---|---|---|---|---|---|---|---|
| Phe | Ser | Leu | Asp | Asp | Leu | Gln | Pro | Trp | His | Ser | Phe | Gly | Ala | Asp | Ser |  |
|  |  |  | 540 |  |  |  |  | 545 |  |  |  |  | 550 |  |  |  |

| GTG | CCA | GCC | AAC | ACA | GAA | AAC | GAA | GTT | GAG | CCT | GTT | GAT | GCC | CGC | CCT | 1853 |
|---|---|---|---|---|---|---|---|---|---|---|---|---|---|---|---|---|
| Val | Pro | Ala | Asn | Thr | Glu | Asn | Glu | Val | Glu | Pro | Val | Asp | Ala | Arg | Pro |  |
|  | 555 |  |  |  |  | 560 |  |  |  |  | 565 |  |  |  |  |  |

| GCT | GCC | GAC | CGA | GGA | CTG | ACC | ACT | CGA | CCA | GGT | TCT | GGG | TTG | ACA | AAT | 1901 |
|---|---|---|---|---|---|---|---|---|---|---|---|---|---|---|---|---|
| Ala | Ala | Asp | Arg | Gly | Leu | Thr | Thr | Arg | Pro | Gly | Ser | Gly | Leu | Thr | Asn |  |
| 570 |  |  |  |  | 575 |  |  |  |  | 580 |  |  |  |  | 585 |  |

| ATC | AAG | ACG | GAG | GAG | ATC | TCT | GAA | GTG | AAG | ATG | GAT | GCA | GAA | TTC | CGA | 1949 |
|---|---|---|---|---|---|---|---|---|---|---|---|---|---|---|---|---|
| Ile | Lys | Thr | Glu | Glu | Ile | Ser | Glu | Val | Lys | Met | Asp | Ala | Glu | Phe | Arg |  |
|  |  |  |  | 590 |  |  |  |  | 595 |  |  |  |  | 600 |  |  |

| CAT | GAC | TCA | GGA | TAT | GAA | GTT | CAT | CAT | CAA | AAA | TTG | GTG | TTC | TTT | GCA | 1997 |
|---|---|---|---|---|---|---|---|---|---|---|---|---|---|---|---|---|
| His | Asp | Ser | Gly | Tyr | Glu | Val | His | His | Gln | Lys | Leu | Val | Phe | Phe | Ala |  |
|  |  | 605 |  |  |  |  | 610 |  |  |  |  | 615 |  |  |  |  |

| GAA | GAT | GTG | GGT | TCA | AAC | AAA | GGT | GCA | ATC | ATT | GGA | CTC | ATG | GTG | GGC | 2045 |
|---|---|---|---|---|---|---|---|---|---|---|---|---|---|---|---|---|
| Glu | Asp | Val | Gly | Ser | Asn | Lys | Gly | Ala | Ile | Ile | Gly | Leu | Met | Val | Gly |  |
|  |  | 620 |  |  |  |  | 625 |  |  |  |  | 630 |  |  |  |  |

| GGT | GTT | GTC | ATA | GCG | ACA | GTG | ATC | GTC | ATC | ACC | TTG | GTG | ATG | CTG | AAG | 2093 |
|---|---|---|---|---|---|---|---|---|---|---|---|---|---|---|---|---|

```
Gly Val Val Ile Ala Thr Val Ile Val Ile Thr Leu Val Met Leu Lys
    635                 640                 645

AAG AAA CAG TAC ACA TCC ATT CAT CAT GGT GTG GTG GAG GTT GAC GCC            2141
Lys Lys Gln Tyr Thr Ser Ile His His Gly Val Val Glu Val Asp Ala
650             655                 660                 665

GCT GTC ACC CCA GAG GAG CGC CAC CTG TCC AAG ATG CAG CAG AAC GGC            2189
Ala Val Thr Pro Glu Glu Arg His Leu Ser Lys Met Gln Gln Asn Gly
            670                 675                 680

TAC GAA AAT CCA ACC TAC AAG TTC TTT GAG CAG ATG CAG AAC                    2231
Tyr Glu Asn Pro Thr Tyr Lys Phe Phe Glu Gln Met Gln Asn
                685                 690             695

TAGACCCCG CCACAGCAGC CTCTGAAGTT GGACAGCAAA ACCATTGCTT CACTACCCAT           2291

CGGTGTCCAT TTATAGAATA ATGTGGGAAG AAACAAACCC GTTTATGAT TTACTCATTA           2351

TCGCCTTTTG ACAGCTGTGC TGTAACACAA GTAGATGCCT GAACTTGAAT TAATCCACAC          2411

ATCAGTAATG TATTCTATCT CTCTTACAT TTTGGTCTCT ATACTACATT ATTAATGGGT           2471

TTTGTGTACT GTAAAGAATT TAGCTGTATC AAACTAGTGC ATGAATAGAT TCTCTCCTGA          2531

TTATTTATCA CATAGCCCCT TAGCCAGTTG TATATTATTC TTGTGGTTTG TGACCCAATT          2591

AAGTCCTACT TTACATATGC TTTAAGAATC GATGGGGGAT GCTTCATGTG AACGTGGGAG          2651

TTCAGCTGCT TCTCTTGCCT AAGTATTCCT TTCCTGATCA CTATGCATTT TAAAGTTAAA         2711

CATTTTTAAG TATTTCAGAT GCTTTAGAGA GATTTTTTTT CCATGACTGC ATTTACTGT          2771

ACAGATTGCT GCTTCTGCTA TATTTGTGAT ATAGGAATTA AGAGGATACA CACGTTTGTT          2831

TCTTCGTGCC TGTTTTATGT GCACACATTA GGCATTGAGA CTTCAAGCTT TTCTTTTTTT         2891

GTCCACGTAT CTTTGGGTCT TTGATAAAGA AAAGAATCCC TGTTCATTGT AAGCACTTTT         2951

ACGGGGCGGG TGGGGAGGGG TGCTCTGCTG GTCTTCAATT ACCAAGAATT CTCCAAAACA         3011

ATTTTCTGCA GGATGATTGT ACAGAATCAT TGCTTATGAC ATGATCGCTT TCTACACTGT          3071

ATTACATAAA TAAATTAAAT AAAATAACCC CGGGCAAGAC TTTTCTTTGA AGGATGACTA         3131

CAGACATTAA ATAATCGAAG TAATTTTGGG TGGGGAGAAG AGGCAGATTC AATTTTCTTT         3191

AACCAGTCTG AAGTTTCATT TATGATACAA AAGAAGATGA AATGGAAGT GGCAATATAA          3251

GGGGATGAGG AAGGCATGCC TGGACAAACC CTTCTTTTAA GATGTGTCTT CAATTTGTAT         3311

AAAATGGTGT TTTCATGTAA ATAAATACAT TCTTGGAGGA GC                            3353
```

( 2 ) INFORMATION FOR SEQ ID NO:2:

( i ) SEQUENCE CHARACTERISTICS:
        ( A ) LENGTH: 695 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Leu Pro Gly Leu Ala Leu Leu Leu Ala Ala Trp Thr Ala Arg
 1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80
```

```
Gln  Ile  Thr  Asn  Val  Val  Glu  Ala  Asn  Gln  Pro  Val  Thr  Ile  Gln  Asn
               85                  90                            95

Trp  Cys  Lys  Arg  Gly  Arg  Lys  Gln  Cys  Lys  Thr  His  Pro  His  Phe  Val
              100                 105                      110

Ile  Pro  Tyr  Arg  Cys  Leu  Val  Gly  Glu  Phe  Val  Ser  Asp  Ala  Leu  Leu
              115                 120                      125

Val  Pro  Asp  Lys  Cys  Lys  Phe  Leu  His  Gln  Glu  Arg  Met  Asp  Val  Cys
              130                 135                      140

Glu  Thr  His  Leu  His  Trp  His  Thr  Val  Ala  Lys  Glu  Thr  Cys  Ser  Glu
145                      150                 155                           160

Lys  Ser  Thr  Asn  Leu  His  Asp  Tyr  Gly  Met  Leu  Leu  Pro  Cys  Gly  Ile
              165                 170                      175

Asp  Lys  Phe  Arg  Gly  Val  Glu  Phe  Val  Cys  Cys  Pro  Leu  Ala  Glu  Glu
              180                 185                      190

Ser  Asp  Asn  Val  Asp  Ser  Ala  Asp  Ala  Glu  Glu  Asp  Asp  Ser  Asp  Val
              195                 200                      205

Trp  Trp  Gly  Gly  Ala  Asp  Thr  Asp  Tyr  Ala  Asp  Gly  Ser  Glu  Asp  Lys
     210                 215                      220

Val  Val  Glu  Val  Ala  Glu  Glu  Glu  Val  Ala  Glu  Val  Glu  Glu  Glu  Glu
225                      230                 235                           240

Glu  Ala  Asp  Asp  Asp  Glu  Asp  Asp  Glu  Asp  Gly  Asp  Glu  Val  Glu  Glu
              245                 250                      255

Glu  Ala  Glu  Glu  Pro  Tyr  Glu  Glu  Ala  Thr  Glu  Arg  Thr  Thr  Ser  Ile
              260                 265                      270

Ala  Thr  Thr  Thr  Thr  Thr  Thr  Thr  Glu  Ser  Val  Glu  Glu  Val  Val  Arg
              275                 280                      285

Val  Pro  Thr  Thr  Ala  Ala  Ser  Thr  Pro  Asp  Ala  Val  Asp  Lys  Tyr  Leu
     290                 295                      300

Glu  Thr  Pro  Gly  Asp  Glu  Asn  Glu  His  Ala  His  Phe  Gln  Lys  Ala  Lys
305                      310                 315                           320

Glu  Arg  Leu  Glu  Ala  Lys  His  Arg  Glu  Arg  Met  Ser  Gln  Val  Met  Arg
              325                 330                      335

Glu  Trp  Glu  Glu  Ala  Glu  Arg  Gln  Ala  Lys  Asn  Leu  Pro  Lys  Ala  Asp
              340                 345                      350

Lys  Lys  Ala  Val  Ile  Gln  His  Phe  Gln  Glu  Lys  Val  Glu  Ser  Leu  Glu
              355                 360                      365

Gln  Glu  Ala  Ala  Asn  Glu  Arg  Gln  Gln  Leu  Val  Glu  Thr  His  Met  Ala
370                      375                 380

Arg  Val  Glu  Ala  Met  Leu  Asn  Asp  Arg  Arg  Arg  Leu  Ala  Leu  Glu  Asn
385                      390                 395                           400

Tyr  Ile  Thr  Ala  Leu  Gln  Ala  Val  Pro  Pro  Arg  Pro  Arg  His  Val  Phe
              405                 410                      415

Asn  Met  Leu  Lys  Lys  Tyr  Val  Arg  Ala  Glu  Gln  Lys  Asp  Arg  Gln  His
              420                 425                      430

Thr  Leu  Lys  His  Phe  Glu  His  Val  Arg  Met  Val  Asp  Pro  Lys  Lys  Ala
              435                 440                      445

Ala  Gln  Ile  Arg  Ser  Gln  Val  Met  Thr  His  Leu  Arg  Val  Ile  Tyr  Glu
     450                 455                      460

Arg  Met  Asn  Gln  Ser  Leu  Ser  Leu  Leu  Tyr  Asn  Val  Pro  Ala  Val  Ala
465                      470                 475                           480

Glu  Glu  Ile  Gln  Asp  Glu  Val  Asp  Glu  Leu  Leu  Gln  Lys  Glu  Gln  Asn
              485                 490                      495

Tyr  Ser  Asp  Asp  Val  Leu  Ala  Asn  Met  Ile  Ser  Glu  Pro  Arg  Ile  Ser
              500                 505                      510
```

```
Tyr Gly Asn Asp Ala Leu Met Pro Ser Leu Thr Glu Thr Lys Thr Thr
        515                 520                 525
Val Glu Leu Leu Pro Val Asn Gly Glu Phe Ser Leu Asp Asp Leu Gln
    530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Met Asp Ala Glu Phe Arg His Asp Ser Gly Tyr Glu Val
        595                 600                 605
His His Gln Lys Leu Val Phe Phe Ala Glu Asp Val Gly Ser Asn Lys
    610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
        675                 680                 685
Phe Phe Glu Gln Met Gln Asn
    690                 695
```

( 2 ) INFORMATION FOR SEQ ID NO:3:

( i ) SEQUENCE CHARACTERISTICS:
        ( A ) LENGTH: 3148 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 125..2377

( x i ) SEQUENCE DESCRIPTION: SEQ ID NO:3:

```
GAATTCCCGC GGAGCAGCGT GCGCGGGGCC CCGGGAGACG GCGGCGGTAG CGGCGCGGGC        60

AGAGCAAGGA CGCGGCGGAT CCCACTCGCA CAGCAGCGCA CTCGGTGCCC CGCGCAGGGT       120

CGCG ATG CTG CCC GGT TTG GCA CTG CTC CTG CTG GCC GCC TGG ACG GCT       169
     Met Leu Pro Gly Leu Ala Leu Leu Leu Leu Ala Ala Trp Thr Ala
      1               5                  10                  15

CGG GCG CTG GAG GTA CCC ACT GAT GGT AAT GCT GGC CTG CTG GCT GAA       217
Arg Ala Leu Glu Val Pro Thr Asp Gly Asn Ala Gly Leu Leu Ala Glu
             20                  25                  30

CCC CAG ATT GCC ATG TTC TGT GGC AGA CTG AAC ATG CAC ATG AAT GTC       265
Pro Gln Ile Ala Met Phe Cys Gly Arg Leu Asn Met His Met Asn Val
                 35                  40                  45

CAG AAT GGG AAG TGG GAT TCA GAT CCA TCA GGG ACC AAA ACC TGC ATT       313
Gln Asn Gly Lys Trp Asp Ser Asp Pro Ser Gly Thr Lys Thr Cys Ile
         50                  55                  60

GAT ACC AAG GAA GGC ATC CTG CAG TAT TGC CAA GAA GTC TAC CCT GAA       361
Asp Thr Lys Glu Gly Ile Leu Gln Tyr Cys Gln Glu Val Tyr Pro Glu
 65                  70                  75

CTG CAG ATC ACC AAT GTG GTA GAA GCC AAC CAA CCA GTG ACC ATC CAG       409
Leu Gln Ile Thr Asn Val Val Glu Ala Asn Gln Pro Val Thr Ile Gln
```

```
                          80                         85                         90                         95
AAC   TGG   TGC   AAG   CGG   GGC   CGC   AAG   CAG   TGC   AAG   ACC   CAT   CCC   CAC   TTT        457
Asn   Trp   Cys   Lys   Arg   Gly   Arg   Lys   Gln   Cys   Lys   Thr   His   Pro   His   Phe
                        100                         105                         110

GTG   ATT   CCC   TAC   CGC   TGC   TTA   GTT   GGT   GAG   TTT   GTA   AGT   GAT   GCC   CTT        505
Val   Ile   Pro   Tyr   Arg   Cys   Leu   Val   Gly   Glu   Phe   Val   Ser   Asp   Ala   Leu
                        115                         120                         125

CTC   GTT   CCT   GAC   AAG   TGC   AAA   TTC   TTA   CAC   CAG   GAG   AGG   ATG   GAT   GTT        553
Leu   Val   Pro   Asp   Lys   Cys   Lys   Phe   Leu   His   Gln   Glu   Arg   Met   Asp   Val
                  130                         135                         140

TGC   GAA   ACT   CAT   CTT   CAC   TGG   CAC   ACC   GTC   GCC   AAA   GAG   ACA   TGC   AGT        601
Cys   Glu   Thr   His   Leu   His   Trp   His   Thr   Val   Ala   Lys   Glu   Thr   Cys   Ser
            145                         150                         155

GAG   AAG   AGT   ACC   AAC   TTG   CAT   GAC   TAC   GGC   ATG   TTG   CTG   CCC   TGC   GGA        649
Glu   Lys   Ser   Thr   Asn   Leu   His   Asp   Tyr   Gly   Met   Leu   Leu   Pro   Cys   Gly
160                         165                         170                         175

ATT   GAC   AAG   TTC   CGA   GGG   GTA   GAG   TTT   GTG   TGT   TGC   CCA   CTG   GCT   GAA        697
Ile   Asp   Lys   Phe   Arg   Gly   Val   Glu   Phe   Val   Cys   Cys   Pro   Leu   Ala   Glu
                        180                         185                         190

GAA   AGT   GAC   AAT   GTG   GAT   TCT   GCT   GAT   GCG   GAG   GAG   GAT   GAC   TCG   GAT        745
Glu   Ser   Asp   Asn   Val   Asp   Ser   Ala   Asp   Ala   Glu   Glu   Asp   Asp   Ser   Asp
                  195                         200                         205

GTC   TGG   TGG   GGC   GGA   GCA   GAC   ACA   GAC   TAT   GCA   GAT   GGG   AGT   GAA   GAC        793
Val   Trp   Trp   Gly   Gly   Ala   Asp   Thr   Asp   Tyr   Ala   Asp   Gly   Ser   Glu   Asp
            210                         215                         220

AAA   GTA   GTA   GAA   GTA   GCA   GAG   GAG   GAA   GAA   GTG   GCT   GAG   GTG   GAA   GAA        841
Lys   Val   Val   Glu   Val   Ala   Glu   Glu   Glu   Glu   Val   Ala   Glu   Val   Glu   Glu
225                         230                         235

GAA   GAA   GCC   GAT   GAT   GAC   GAG   GAC   GAT   GAG   GAT   GGT   GAT   GAG   GTA   GAG        889
Glu   Glu   Ala   Asp   Asp   Asp   Glu   Asp   Asp   Glu   Asp   Gly   Asp   Glu   Val   Glu
240                         245                         250                         255

GAA   GAG   GCT   GAG   GAA   CCC   TAC   GAA   GAA   GCC   ACA   GAG   AGA   ACC   ACC   AGC        937
Glu   Glu   Ala   Glu   Glu   Pro   Tyr   Glu   Glu   Ala   Thr   Glu   Arg   Thr   Thr   Ser
                        260                         265                         270

ATT   GCC   ACC   ACC   ACC   ACC   ACC   ACA   GAG   TCT   GTG   GAA   GAG   GTG   GTT           985
Ile   Ala   Thr   Thr   Thr   Thr   Thr   Thr   Glu   Ser   Val   Glu   Glu   Val   Val
                  275                         280                         285

CGA   GAG   GTG   TGC   TCT   GAA   CAA   GCC   GAG   ACG   GGG   CCG   TGC   CGA   GCA   ATG       1033
Arg   Glu   Val   Cys   Ser   Glu   Gln   Ala   Glu   Thr   Gly   Pro   Cys   Arg   Ala   Met
            290                         295                         300

ATC   TCC   CGC   TGG   TAC   TTT   GAT   GTG   ACT   GAA   GGG   AAG   TGT   GCC   CCA   TTC       1081
Ile   Ser   Arg   Trp   Tyr   Phe   Asp   Val   Thr   Glu   Gly   Lys   Cys   Ala   Pro   Phe
      305                         310                         315

TTT   TAC   GGC   GGA   TGT   GGC   GGC   AAC   CGG   AAC   AAC   TTT   GAC   ACA   GAA   GAG       1129
Phe   Tyr   Gly   Gly   Cys   Gly   Gly   Asn   Arg   Asn   Asn   Phe   Asp   Thr   Glu   Glu
320                         325                         330                         335

TAC   TGC   ATG   GCC   GTG   TGT   GGC   AGC   GCC   ATT   CCT   ACA   ACA   GCA   GCC   AGT       1177
Tyr   Cys   Met   Ala   Val   Cys   Gly   Ser   Ala   Ile   Pro   Thr   Thr   Ala   Ala   Ser
                        340                         345                         350

ACC   CCT   GAT   GCC   GTT   GAC   AAG   TAT   CTC   GAG   ACA   CCT   GGG   GAT   GAG   AAT       1225
Thr   Pro   Asp   Ala   Val   Asp   Lys   Tyr   Leu   Glu   Thr   Pro   Gly   Asp   Glu   Asn
            355                         360                         365

GAA   CAT   GCC   CAT   TTC   CAG   AAA   GCC   AAA   GAG   AGG   CTT   GAG   GCC   AAG   CAC       1273
Glu   His   Ala   His   Phe   Gln   Lys   Ala   Lys   Glu   Arg   Leu   Glu   Ala   Lys   His
            370                         375                         380

CGA   GAG   AGA   ATG   TCC   CAG   GTC   ATG   AGA   GAA   TGG   GAA   GAG   GCA   GAA   CGT       1321
Arg   Glu   Arg   Met   Ser   Gln   Val   Met   Arg   Glu   Trp   Glu   Glu   Ala   Glu   Arg
385                         390                         395

CAA   GCA   AAG   AAC   TTG   CCT   AAA   GCT   GAT   AAG   AAG   GCA   GTT   ATC   CAG   CAT       1369
Gln   Ala   Lys   Asn   Leu   Pro   Lys   Ala   Asp   Lys   Lys   Ala   Val   Ile   Gln   His
```

| | | | | | | | | | | | | | | | | |
|---|---|---|---|---|---|---|---|---|---|---|---|---|---|---|---|---|
| | | 400 | | | | 405 | | | | 410 | | | | 415 | | |
| TTC | CAG | GAG | AAA | GTG | GAA | TCT | TTG | GAA | CAG | GAA | GCA | GCC | AAC | GAG | AGA | 1417 |
| Phe | Gln | Glu | Lys | Val | Glu | Ser | Leu | Glu | Gln | Glu | Ala | Ala | Asn | Glu | Arg | |
| | | | | 420 | | | | 425 | | | | | 430 | | | |
| CAG | CAG | CTG | GTG | GAG | ACA | CAC | ATG | GCC | AGA | GTG | GAA | GCC | ATG | CTC | AAT | 1465 |
| Gln | Gln | Leu | Val | Glu | Thr | His | Met | Ala | Arg | Val | Glu | Ala | Met | Leu | Asn | |
| | | | 435 | | | | | 440 | | | | | 445 | | | |
| GAC | CGC | CGC | CGC | CTG | GCC | CTG | GAG | AAC | TAC | ATC | ACC | GCT | CTG | CAG | GCT | 1513 |
| Asp | Arg | Arg | Arg | Leu | Ala | Leu | Glu | Asn | Tyr | Ile | Thr | Ala | Leu | Gln | Ala | |
| | | 450 | | | | | 455 | | | | | 460 | | | | |
| GTT | CCT | CCT | CGG | CCT | CGT | CAC | GTG | TTC | AAT | ATG | CTA | AAG | AAG | TAT | GTC | 1561 |
| Val | Pro | Pro | Arg | Pro | Arg | His | Val | Phe | Asn | Met | Leu | Lys | Lys | Tyr | Val | |
| | 465 | | | | | 470 | | | | | 475 | | | | | |
| CGC | GCA | GAA | CAG | AAG | GAC | AGA | CAG | CAC | ACC | CTA | AAG | CAT | TTC | GAG | CAT | 1609 |
| Arg | Ala | Glu | Gln | Lys | Asp | Arg | Gln | His | Thr | Leu | Lys | His | Phe | Glu | His | |
| 480 | | | | | 485 | | | | | 490 | | | | | 495 | |
| GTG | CGC | ATG | GTG | GAT | CCC | AAG | AAA | GCC | GCT | CAG | ATC | CGG | TCC | CAG | GTT | 1657 |
| Val | Arg | Met | Val | Asp | Pro | Lys | Lys | Ala | Ala | Gln | Ile | Arg | Ser | Gln | Val | |
| | | | | 500 | | | | | 505 | | | | | 510 | | |
| ATG | ACA | CAC | CTC | CGT | GTG | ATT | TAT | GAG | CGC | ATG | AAT | CAG | TCT | CTC | TCC | 1705 |
| Met | Thr | His | Leu | Arg | Val | Ile | Tyr | Glu | Arg | Met | Asn | Gln | Ser | Leu | Ser | |
| | | | 515 | | | | | 520 | | | | | 525 | | | |
| CTG | CTC | TAC | AAC | GTG | CCT | GCA | GTG | GCC | GAG | GAG | ATT | CAG | GAT | GAA | GTT | 1753 |
| Leu | Leu | Tyr | Asn | Val | Pro | Ala | Val | Ala | Glu | Glu | Ile | Gln | Asp | Glu | Val | |
| | | 530 | | | | | 535 | | | | | 540 | | | | |
| GAT | GAG | CTG | CTT | CAG | AAA | GAG | CAA | AAC | TAT | TCA | GAT | GAC | GTC | TTG | GCC | 1801 |
| Asp | Glu | Leu | Leu | Gln | Lys | Glu | Gln | Asn | Tyr | Ser | Asp | Asp | Val | Leu | Ala | |
| | 545 | | | | | 550 | | | | | 555 | | | | | |
| AAC | ATG | ATT | AGT | GAA | CCA | AGG | ATC | AGT | TAC | GGA | AAC | GAT | GCT | CTC | ATG | 1849 |
| Asn | Met | Ile | Ser | Glu | Pro | Arg | Ile | Ser | Tyr | Gly | Asn | Asp | Ala | Leu | Met | |
| 560 | | | | | 565 | | | | | 570 | | | | | 575 | |
| CCA | TCT | TTG | ACC | GAA | ACG | AAA | ACC | ACC | GTG | GAG | CTC | CTT | CCC | GTG | AAT | 1897 |
| Pro | Ser | Leu | Thr | Glu | Thr | Lys | Thr | Thr | Val | Glu | Leu | Leu | Pro | Val | Asn | |
| | | | | 580 | | | | | 585 | | | | | 590 | | |
| GGA | GAG | TTC | AGC | CTG | GAC | GAT | CTC | CAG | CCG | TGG | CAT | TCT | TTT | GGG | GCT | 1945 |
| Gly | Glu | Phe | Ser | Leu | Asp | Asp | Leu | Gln | Pro | Trp | His | Ser | Phe | Gly | Ala | |
| | | | 595 | | | | | 600 | | | | | 605 | | | |
| GAC | TCT | GTG | CCA | GCC | AAC | ACA | GAA | AAC | GAA | GTT | GAG | CCT | GTT | GAT | GCC | 1993 |
| Asp | Ser | Val | Pro | Ala | Asn | Thr | Glu | Asn | Glu | Val | Glu | Pro | Val | Asp | Ala | |
| | | 610 | | | | | 615 | | | | | 620 | | | | |
| CGC | CCT | GCT | GCC | GAC | CGA | GGA | CTG | ACC | ACT | CGA | CCA | GGT | TCT | GGG | TTG | 2041 |
| Arg | Pro | Ala | Ala | Asp | Arg | Gly | Leu | Thr | Thr | Arg | Pro | Gly | Ser | Gly | Leu | |
| | 625 | | | | | 630 | | | | | 635 | | | | | |
| ACA | AAT | ATC | AAG | ACG | GAG | GAG | ATC | TCT | GAA | GTG | AAG | ATG | GAT | GCA | GAA | 2089 |
| Thr | Asn | Ile | Lys | Thr | Glu | Glu | Ile | Ser | Glu | Val | Lys | Met | Asp | Ala | Glu | |
| 640 | | | | | 645 | | | | | 650 | | | | | 655 | |
| TTC | CGA | CAT | GAC | TCA | GGA | TAT | GAA | GTT | CAT | CAT | CAA | AAA | TTG | GTG | TTC | 2137 |
| Phe | Arg | His | Asp | Ser | Gly | Tyr | Glu | Val | His | His | Gln | Lys | Leu | Val | Phe | |
| | | | | 660 | | | | | 665 | | | | | 670 | | |
| TTT | GCA | GAA | GAT | GTG | GGT | TCA | AAC | AAA | GGT | GCA | ATC | ATT | GGA | CTC | ATG | 2185 |
| Phe | Ala | Glu | Asp | Val | Gly | Ser | Asn | Lys | Gly | Ala | Ile | Ile | Gly | Leu | Met | |
| | | | 675 | | | | | 680 | | | | | 685 | | | |
| GTG | GGC | GGT | GTT | GTC | ATA | GCG | ACA | GTG | ATC | GTC | ATC | ACC | TTG | GTG | ATG | 2233 |
| Val | Gly | Gly | Val | Val | Ile | Ala | Thr | Val | Ile | Val | Ile | Thr | Leu | Val | Met | |
| | | 690 | | | | | 695 | | | | | 700 | | | | |
| CTG | AAG | AAG | AAA | CAG | TAC | ACA | TCC | ATT | CAT | CAT | GGT | GTG | GTG | GAG | GTT | 2281 |
| Leu | Lys | Lys | Lys | Gln | Tyr | Thr | Ser | Ile | His | His | Gly | Val | Val | Glu | Val | |
| | 705 | | | | | 710 | | | | | 715 | | | | | |
| GAC | GCC | GCT | GTC | ACC | CCA | GAG | GAG | CGC | CAC | CTG | TCC | AAG | ATG | CAG | CAG | 2329 |
| Asp | Ala | Ala | Val | Thr | Pro | Glu | Glu | Arg | His | Leu | Ser | Lys | Met | Gln | Gln | |

| | | | | | | | | | | | | | | | |
|---|---|---|---|---|---|---|---|---|---|---|---|---|---|---|---|
|720| | | | |725| | | | |730| | | | |735|

```
AAC  GGC  TAC  GAA  AAT  CCA  ACC  TAC  AAG  TTC  TTT  GAG  CAG  ATG  CAG  AAC        2377
Asn  Gly  Tyr  Glu  Asn  Pro  Thr  Tyr  Lys  Phe  Phe  Glu  Gln  Met  Gln  Asn
                         740                 745                      750

TAGACCCCCG CCACAGCAGC CTCTGAAGTT GGACAGCAAA ACCATTGCTT CACTACCCAT    2437
CGGTGTCCAT TTATAGAATA ATGTGGGAAG AAACAAACCC GTTTTATGAT TTACTCATTA    2497
TCGCCTTTTG ACAGCTGTGC TGTAACACAA GTAGATGCCT GAACTTGAAT TAATCCACAC    2557
ATCAGTAATG TATTCTATCT CTCTTTACAT TTGGTCTCT  ATACTACATT ATTAATGGGT    2617
TTTGTGTACT GTAAAGAATT TAGCTGTATC AAACTAGTGC ATGAATAGAT TCTCTCCTGA    2677
TTATTTATCA CATAGCCCCT TAGCCAGTTG TATATTATTC TTGTGGTTTG TGACCCAATT    2737
AAGTCCTACT TTACATATGC TTTAAGAATC GATGGGGGAT GCTTCATGTG AACGTGGGAG    2797
TTCAGCTGCT TCTCTTGCCT AAGTATTCCT TTCCTGATCA CTATGCATTT TAAAGTAAA     2857
CATTTTTAAG TATTTCAGAT GCTTAGAGA  GATTTTTTT  CCATGACTGC ATTTTACTGT    2917
ACAGATTGCT GCTTCTGCTA TATTTGTGAT ATAGGAATTA AGAGGATACA CACGTTTGTT    2977
TCTTCGTGCC TGTTTTATGT GCACACATTA GGCATTGAGA CTTCAAGCTT TTCTTTTTT     3037
GTCCACGTAT CTTTGGGTCT TTGATAAAGA AAAGAATCCC TGTTCATTGT AAGCACTTTT    3097
ACGGGGCGGG TGGGAGGGG  TGCTCTGCTG GTCTTCAATT ACCAAGAATT C             3148
```

( 2 ) INFORMATION FOR SEQ ID NO:4:

( i ) SEQUENCE CHARACTERISTICS:
        ( A ) LENGTH: 751 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Leu  Pro  Gly  Leu  Ala  Leu  Leu  Leu  Ala  Ala  Trp  Thr  Ala  Arg
 1               5                   10                       15

Ala  Leu  Glu  Val  Pro  Thr  Asp  Gly  Asn  Ala  Gly  Leu  Leu  Ala  Glu  Pro
              20                  25                      30

Gln  Ile  Ala  Met  Phe  Cys  Gly  Arg  Leu  Asn  Met  His  Met  Asn  Val  Gln
              35                  40                      45

Asn  Gly  Lys  Trp  Asp  Ser  Asp  Pro  Ser  Gly  Thr  Lys  Thr  Cys  Ile  Asp
      50                  55                      60

Thr  Lys  Glu  Gly  Ile  Leu  Gln  Tyr  Cys  Gln  Glu  Val  Tyr  Pro  Glu  Leu
 65                  70                      75                       80

Gln  Ile  Thr  Asn  Val  Val  Glu  Ala  Asn  Gln  Pro  Val  Thr  Ile  Gln  Asn
              85                  90                      95

Trp  Cys  Lys  Arg  Gly  Arg  Lys  Gln  Cys  Lys  Thr  His  Pro  His  Phe  Val
             100                 105                     110

Ile  Pro  Tyr  Arg  Cys  Leu  Val  Gly  Glu  Phe  Val  Ser  Asp  Ala  Leu  Leu
             115                 120                     125

Val  Pro  Asp  Lys  Cys  Lys  Phe  Leu  His  Gln  Glu  Arg  Met  Asp  Val  Cys
             130                 135                     140

Glu  Thr  His  Leu  His  Trp  His  Thr  Val  Ala  Lys  Glu  Thr  Cys  Ser  Glu
145                  150                     155                      160

Lys  Ser  Thr  Asn  Leu  His  Asp  Tyr  Gly  Met  Leu  Leu  Pro  Cys  Gly  Ile
             165                 170                     175

Asp  Lys  Phe  Arg  Gly  Val  Glu  Phe  Val  Cys  Cys  Pro  Leu  Ala  Glu  Glu
             180                 185                     190
```

```
Ser  Asp  Asn  Val  Asp  Ser  Ala  Asp  Ala  Glu  Glu  Asp  Asp  Ser  Asp  Val
          195                      200                      205

Trp  Trp  Gly  Gly  Ala  Asp  Thr  Asp  Tyr  Ala  Asp  Gly  Ser  Glu  Asp  Lys
     210                      215                      220

Val  Val  Glu  Val  Ala  Glu  Glu  Glu  Val  Ala  Glu  Val  Glu  Glu  Glu
225                           230                     235                      240

Glu  Ala  Asp  Asp  Asp  Glu  Asp  Asp  Glu  Asp  Gly  Asp  Glu  Val  Glu  Glu
                    245                      250                      255

Glu  Ala  Glu  Glu  Pro  Tyr  Glu  Glu  Ala  Thr  Glu  Arg  Thr  Thr  Ser  Ile
               260                      265                      270

Ala  Thr  Thr  Thr  Thr  Thr  Thr  Glu  Ser  Val  Glu  Glu  Val  Val  Arg
          275                      280                      285

Glu  Val  Cys  Ser  Glu  Gln  Ala  Glu  Thr  Gly  Pro  Cys  Arg  Ala  Met  Ile
     290                      295                      300

Ser  Arg  Trp  Tyr  Phe  Asp  Val  Thr  Glu  Gly  Lys  Cys  Ala  Pro  Phe  Phe
305                      310                      315                      320

Tyr  Gly  Gly  Cys  Gly  Gly  Asn  Arg  Asn  Asn  Phe  Asp  Thr  Glu  Glu  Tyr
                    325                      330                      335

Cys  Met  Ala  Val  Cys  Gly  Ser  Ala  Ile  Pro  Thr  Thr  Ala  Ala  Ser  Thr
               340                      345                      350

Pro  Asp  Ala  Val  Asp  Lys  Tyr  Leu  Glu  Thr  Pro  Gly  Asp  Glu  Asn  Glu
          355                      360                      365

His  Ala  His  Phe  Gln  Lys  Ala  Lys  Glu  Arg  Leu  Glu  Ala  Lys  His  Arg
     370                      375                      380

Glu  Arg  Met  Ser  Gln  Val  Met  Arg  Glu  Trp  Glu  Ala  Glu  Arg  Gln
385                      390                      395                      400

Ala  Lys  Asn  Leu  Pro  Lys  Ala  Asp  Lys  Lys  Ala  Val  Ile  Gln  His  Phe
               405                      410                      415

Gln  Glu  Lys  Val  Glu  Ser  Leu  Glu  Gln  Glu  Ala  Ala  Asn  Glu  Arg  Gln
          420                      425                      430

Gln  Leu  Val  Glu  Thr  His  Met  Ala  Arg  Val  Glu  Ala  Met  Leu  Asn  Asp
          435                      440                      445

Arg  Arg  Arg  Leu  Ala  Leu  Glu  Asn  Tyr  Ile  Thr  Ala  Leu  Gln  Ala  Val
     450                      455                      460

Pro  Pro  Arg  Pro  Arg  His  Val  Phe  Asn  Met  Leu  Lys  Lys  Tyr  Val  Arg
465                      470                      475                      480

Ala  Glu  Gln  Lys  Asp  Arg  Gln  His  Thr  Leu  Lys  His  Phe  Glu  His  Val
               485                      490                      495

Arg  Met  Val  Asp  Pro  Lys  Lys  Ala  Ala  Gln  Ile  Arg  Ser  Gln  Val  Met
          500                      505                      510

Thr  His  Leu  Arg  Val  Ile  Tyr  Glu  Arg  Met  Asn  Gln  Ser  Leu  Ser  Leu
          515                      520                      525

Leu  Tyr  Asn  Val  Pro  Ala  Val  Ala  Glu  Glu  Ile  Gln  Asp  Glu  Val  Asp
     530                      535                      540

Glu  Leu  Leu  Gln  Lys  Glu  Gln  Asn  Tyr  Ser  Asp  Asp  Val  Leu  Ala  Asn
545                      550                      555                      560

Met  Ile  Ser  Glu  Pro  Arg  Ile  Ser  Tyr  Gly  Asn  Asp  Ala  Leu  Met  Pro
               565                      570                      575

Ser  Leu  Thr  Glu  Thr  Lys  Thr  Thr  Val  Glu  Leu  Leu  Pro  Val  Asn  Gly
          580                      585                      590

Glu  Phe  Ser  Leu  Asp  Asp  Leu  Gln  Pro  Trp  His  Ser  Phe  Gly  Ala  Asp
     595                      600                      605

Ser  Val  Pro  Ala  Asn  Thr  Glu  Asn  Glu  Val  Glu  Pro  Val  Asp  Ala  Arg
     610                      615                      620
```

```
Pro  Ala  Ala  Asp  Arg  Gly  Leu  Thr  Thr  Arg  Pro  Gly  Ser  Gly  Leu  Thr
625            630                           635                           640

Asn  Ile  Lys  Thr  Glu  Glu  Ile  Ser  Glu  Val  Lys  Met  Asp  Ala  Glu  Phe
                645                      650                           655

Arg  His  Asp  Ser  Gly  Tyr  Glu  Val  His  His  Gln  Lys  Leu  Val  Phe  Phe
               660                      665                      670

Ala  Glu  Asp  Val  Gly  Ser  Asn  Lys  Gly  Ala  Ile  Ile  Gly  Leu  Met  Val
          675                      680                      685

Gly  Gly  Val  Val  Ile  Ala  Thr  Val  Ile  Val  Ile  Thr  Leu  Val  Met  Leu
     690                      695                      700

Lys  Lys  Lys  Gln  Tyr  Thr  Ser  Ile  His  His  Gly  Val  Val  Glu  Val  Asp
705                      710                      715                           720

Ala  Ala  Val  Thr  Pro  Glu  Glu  Arg  His  Leu  Ser  Lys  Met  Gln  Gln  Asn
                725                      730                      735

Gly  Tyr  Glu  Asn  Pro  Thr  Tyr  Lys  Phe  Phe  Glu  Gln  Met  Gln  Asn
               740                      745                      750
```

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: CDS
        ( B ) LOCATION: 1..12

( x i ) SEQUENCE DESCRIPTION: SEQ ID NO:5:

```
ATG  CTG  CCC  GGT                                                          12
Met  Leu  Pro  Gly
  1
```

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Leu  Pro  Gly
  1
```

( 2 ) INFORMATION FOR SEQ ID NO:7:

( i ) SEQUENCE CHARACTERISTICS:
        ( A ) LENGTH: 243 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: CDS
        ( B ) LOCATION: 1..243

( x i ) SEQUENCE DESCRIPTION: SEQ ID NO:7:

```
GTT  CGA  GAG  GTG  TGC  TCT  GAA  CAA  GCC  GAG  ACG  GGG  CCG  TGC  CGA  GCA   48
Val  Arg  Glu  Val  Cys  Ser  Glu  Gln  Ala  Glu  Thr  Gly  Pro  Cys  Arg  Ala
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |     |
| ATG | ATC | TCC | CGC | TGG | TAC | TTT | GAT | GTG | ACT | GAA | GGG | AAG | TGT | GCC | CCA | 96  |
| Met | Ile | Ser | Arg | Trp | Tyr | Phe | Asp | Val | Thr | Glu | Gly | Lys | Cys | Ala | Pro |     |
|     |     |     | 20  |     |     |     |     | 25  |     |     |     |     | 30  |     |     |     |
| TTC | TTT | TAC | GGC | GGA | TGT | GGC | GGC | AAC | CGG | AAC | AAC | TTT | GAC | ACA | GAA | 144 |
| Phe | Phe | Tyr | Gly | Gly | Cys | Gly | Gly | Asn | Arg | Asn | Asn | Phe | Asp | Thr | Glu |     |
|     |     | 35  |     |     |     |     | 40  |     |     |     |     | 45  |     |     |     |     |
| GAG | TAC | TGC | ATG | GCC | GTG | TGT | GGC | AGC | GCC | ATG | TCC | CAA | AGT | TTA | CTC | 192 |
| Glu | Tyr | Cys | Met | Ala | Val | Cys | Gly | Ser | Ala | Met | Ser | Gln | Ser | Leu | Leu |     |
|     | 50  |     |     |     |     | 55  |     |     |     |     | 60  |     |     |     |     |     |
| AAG | ACT | ACC | CAG | GAA | CCT | CTT | GCC | CGA | GAT | CCT | GTT | AAA | CTT | CCT | ACA | 240 |
| Lys | Thr | Thr | Gln | Glu | Pro | Leu | Ala | Arg | Asp | Pro | Val | Lys | Leu | Pro | Thr |     |
| 65  |     |     |     |     | 70  |     |     |     |     | 75  |     |     |     |     | 80  |     |
| ACA |     |     |     |     |     |     |     |     |     |     |     |     |     |     |     | 243 |
| Thr |     |     |     |     |     |     |     |     |     |     |     |     |     |     |     |     |

( 2 ) INFORMATION FOR SEQ ID NO:8:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Val | Arg | Glu | Val | Cys | Ser | Glu | Gln | Ala | Glu | Thr | Gly | Pro | Cys | Arg | Ala |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Met | Ile | Ser | Arg | Trp | Tyr | Phe | Asp | Val | Thr | Glu | Gly | Lys | Cys | Ala | Pro |
|     |     |     | 20  |     |     |     |     | 25  |     |     |     |     | 30  |     |     |
| Phe | Phe | Tyr | Gly | Gly | Cys | Gly | Gly | Asn | Arg | Asn | Asn | Phe | Asp | Thr | Glu |
|     |     | 35  |     |     |     |     | 40  |     |     |     |     | 45  |     |     |     |
| Glu | Tyr | Cys | Met | Ala | Val | Cys | Gly | Ser | Ala | Met | Ser | Gln | Ser | Leu | Leu |
|     | 50  |     |     |     |     | 55  |     |     |     |     | 60  |     |     |     |     |
| Lys | Thr | Thr | Gln | Glu | Pro | Leu | Ala | Arg | Asp | Pro | Val | Lys | Leu | Pro | Thr |
| 65  |     |     |     |     | 70  |     |     |     |     | 75  |     |     |     |     | 80  |

Thr ( 2 ) INFORMATION FOR SEQ ID NO:9:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:9:

TGATAGTTAT CCCTGTTCTT CCTCCAAGCC TCTGCCTTGG AGCTATGGAT ACTATAACTA     60

ACTGAAGCTT CTTCTTTCAG GTACCACTG     90

( 2 ) INFORMATION FOR SEQ ID NO:10:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:10:

ACAGTGGAGG CTTGTTAGAT GCTTGTAAAT GCCAGCCCCT GCCTCAAGTA ACAATTGATT 60

CTTTTTGTGT GCTCTCCCAG GTCTACCCTG 90

( 2 ) INFORMATION FOR SEQ ID NO:11:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:11:

TCTATCTTTC CTTGATGTCT TCTGCGGTAA GAACACTGTG ATACAGATGG AATGACGGAA 60

GTGGTTTTCC TTTCTTTCAG TTGGTGAGTT 90

( 2 ) INFORMATION FOR SEQ ID NO:12:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:12:

TTGATTATTT TATGCGGAGT TTTCTTAAAA TGAAACACAT CATCTCTAGC CACTCACTGT 60

TTTCTCCTTA CACTTTGTAG ACATGCAGTG 90

( 2 ) INFORMATION FOR SEQ ID NO:13:

( i ) SEQUENCE CHARACTERISTICS:
        ( A ) LENGTH: 87 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:13:

AAAATTCCAT ATGGACGACT TTTCTTTTTC CTTCCCTGAA ATGTGGTTTA ATTGACTTTT 60

TCTGTTTGCC TTCACAGTGA AGACAAA 87

( 2 ) INFORMATION FOR SEQ ID NO:14:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:14:

AAGAAGTAAA CGTGTATACA TGAACAGAGA GACAGTGCCT TTTCATGCTA AATGTGGTTC 60

CCCACATCTC CTCTGATTAG AGGTGTGCTC 90

( 2 ) INFORMATION FOR SEQ ID NO:15:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:15:

| GTCAGTGGAC | TCGTGCATTT | CACCATCATT | CCCATGTTTC | TCTTTTTGTT | TTTAGTTATG | 60 |
| TTCTCTTATT | TTTTCCATAG | TGTCCCAAAG | | | | 90 |

( 2 ) INFORMATION FOR SEQ ID NO:16:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:16:

| ATACGGCTTT | CTATTAAACG | AGTGGATTAT | TCTGTTGTTG | TTGGCTTTTT | TCTCAAACCT | 60 |
| CCTTCTCTTC | TACTTTATAG | TTCCTACAAC | | | | 90 |

( 2 ) INFORMATION FOR SEQ ID NO:17:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:17:

| ACATAATCAT | CCATCCTATT | AAGTCTGTAT | TCAAAGGATG | AACTGATGAT | TTTAAATTCA | 60 |
| AATGTTTCCT | TAATTTATAG | GTCATGAGAG | | | | 90 |

( 2 ) INFORMATION FOR SEQ ID NO:18:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:18:

| ATGTCTTTTT | TAGAAGACTT | GAAATTGCTG | CTTCATCCTA | CTTATTCAGT | CCCCATGGAC | 60 |
| ATATGTGTTT | ATGATGGCAG | CATTTCCAGG | | | | 90 |

( 2 ) INFORMATION FOR SEQ ID NO:19:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:19:

| TGGAACCTCT | AACCATCGCC | AATGGAAGAA | GCAGTGTTTT | GCACAAACTT | GAAAAAGAGT | 60 |
| TTTTCATTTT | CCTCCCACAG | CCTCGTCACG | | | | 90 |

( 2 ) INFORMATION FOR SEQ ID NO:20:

( i ) SEQUENCE CHARACTERISTICS:
    ( A ) LENGTH: 90 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:20:

```
AAAAAAAAA GAAAAAAAG AAAGAAAAG AACCATTCCT ACCCCCAGAC ATGTGACCTG        60
GAGTGTCATC CTTGATGCAG GTTATGACAC                                      90
```

( 2 ) INFORMATION FOR SEQ ID NO:21:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:21:

```
CAGAAGTAAA TGGTGGCTGC TGCTGCTGCT GCTGTTGTGA TTGTTGTTAC TCACCAAAGA     60
GATGGTTTTG TTTGGTTTAG ATGAGCTGCT                                      90
```

( 2 ) INFORMATION FOR SEQ ID NO:22:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:22:

```
CGACTATGTT TGGGAGCCAC GACTTACCGA TCTTGATTTG TCTTGATTGG CTTTCTGTGT     60
CCCTGGCTTG CCTGTGCCAG TTGAGCCTGT                                      90
```

( 2 ) INFORMATION FOR SEQ ID NO:23:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:23:

```
TAGGCTTTGT CTTACAGTGT TATTATTTAT GAGTAAAACT AATTGGTTGT CCTGCATACT     60
TTAATTATGA TGTAATACAG GTTCTGGGTT                                      90
```

( 2 ) INFORMATION FOR SEQ ID NO:24:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:24:

```
TAGGCTTTGT CTTACAGTGT TATTATTTAT GAGTAAAACT AATTGGTTGT CCTGCATACT     60
```

TTAATTATGA TGTAATACAG GTTCTGGGTT                                                90

( 2 ) INFORMATION FOR SEQ ID NO:25:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:25:

TTATCTTTTT ACTGCTTCTC CATGTTCACC CTTAAAAGAA TGAATTTTAT TTTTTACTCA              60

GCTCTCCTCT TGTTTTTCAG GTTACGCCGC                                                90

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:26:

GGCGCTGGAG GTGGGTGCCG CGCCTCGGAA                                                30

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:27:

TTGCCAAGAA GTAAGTCCTG TCCGGTGGCT                                                30

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:28:

CGCTGCTTAG GTGAGCCGGC CGGCCGAGGG                                                30

( 2 ) INFORMATION FOR SEQ ID NO:29:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:29:

TGCCAAAGAG GTACC                                                                15

( 2 ) INFORMATION FOR SEQ ID NO:30:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:30:

CAGATGGGAG GTAAGGTGGC ATGAATTCCG     30

( 2 ) INFORMATION FOR SEQ ID NO:31:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:31:

GTGGTTCGAG GTAATCCACC ATTTGCTTGG     30

( 2 ) INFORMATION FOR SEQ ID NO:32:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:32:

GGCAGCGCCA GTAAGTGGAC CCTTCTTCGA     30

( 2 ) INFORMATION FOR SEQ ID NO:33:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:33:

CCTGTTAAAC GTACGCGATC ACTGAGGAGG     30

( 2 ) INFORMATION FOR SEQ ID NO:34:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:34:

AATGTCCCAG GTAAGTCTGC TCTTCCATCA     30

( 2 ) INFORMATION FOR SEQ ID NO:35:

( i ) SEQUENCE CHARACTERISTICS:
        ( A ) LENGTH: 30 base pairs
        ( B ) TYPE: nucleic acid ( C ) STRANDEDNESS: double
( D ) TOPOLOGY: linear ( i i ) MOLECULE TYPE: DNA ( x i ) SEQUENCE DESCRIPTION: SEQ ID NO:35:

AGTTATCCAG GTAAAACCTG AACCCATTTC 30

( 2 ) INFORMATION FOR SEQ ID NO:36:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:36:

TCCTCCTCGG GTAGGTCTCG CTGCAGCCGA 30

( 2 ) INFORMATION FOR SEQ ID NO:37:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:37:

CCGGTCCCAG GTAAGCGTGG GGTATAATCA 30

( 2 ) INFORMATION FOR SEQ ID NO:38:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:38:

GATGAAGTTG GTAAGTAAGT GTTCTTTTGA 30

( 2 ) INFORMATION FOR SEQ ID NO:39:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:39:

GAAAACGAAG GTAAGAGTCC CCTGAGCCAG 30

( 2 ) INFORMATION FOR SEQ ID NO:40:

( i ) SEQUENCE CHARACTERISTICS:
    ( A ) LENGTH: 30 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:40:

ACTCGACCAG GTATCAGAAC CGCTTGACGT 30

( 2 ) INFORMATION FOR SEQ ID NO:41:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:41:

TCAAAAATTG GTACGTAAAA TAATTACCCT 30

( 2 ) INFORMATION FOR SEQ ID NO:42:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:42:

TGTGGTGGAG GTAGGTAAAC TTGACTGCAT 30

( 2 ) INFORMATION FOR SEQ ID NO:43:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:43:

TTGGAGGAGC 10

( 2 ) INFORMATION FOR SEQ ID NO:44:

( i ) SEQUENCE CHARACTERISTICS:
        ( A ) LENGTH: 305 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: CDS
        ( B ) LOCATION: 109..255

( i x ) FEATURE:
        ( A ) NAME/KEY: mutation
        ( B ) LOCATION: 193
        ( C ) OTHER INFORMATION: "G can be mutated to T to encode Phe
        rather than Val"

( x i ) SEQUENCE DESCRIPTION: SEQ ID NO:44:

CCAAATGTCC CCGTCATTTA AGAAATGAAA TTCTTCTAAT TGCGTTTATA AATTGTAAAT 60

TATATTGCAT TTAGAAATTA AAATTCTTTT TCTTAATTTG TTTTCAAG GTG TTC TTT 117
                                                                                             Val Phe Phe
                                                                                              1

GCA GAA GAT GTG GGT TCA AAC AAA GGT GCA ATC ATT GGA CTC ATG GTG 165
Ala Glu Asp Val Gly Ser Asn Lys Gly Ala Ile Ile Gly Leu Met Val

```
            5                       10                         15
GGC GGT GTT GTC ATA GCG ACA GTG ATC GTC ATC ACC TTG GTG ATG CTG                    213
Gly Gly Val Val Ile Ala Thr Val Ile Val Ile Thr Leu Val Met Leu
 20              25                  30                   35

AAG AAG AAA CAG TAC ACA TCC ATT CAT CAT GGT GTG GTG GAG GTAGGTAAAC                 265
Lys Lys Lys Gln Tyr Thr Ser Ile His His Gly Val Val Glu
                 40                  45

TTGACTGCAT GTTTCCAAGT GGGAATTAAG ACTATGAGAG                                        305
```

( 2 ) INFORMATION FOR SEQ ID NO:45:

( i ) SEQUENCE CHARACTERISTICS:
        ( A ) LENGTH: 49 amino acids
        ( B ) TYPE: amino acid
        ( D ) TOPOLOGY: linear ( i i ) MOLECULE TYPE: protein ( i x ) FEATURE:
        ( A ) NAME/KEY: mutation
        ( B ) LOCATION: 29
        ( C ) OTHER INFORMATION: "Val can be mutated to be Phe"

( x i ) SEQUENCE DESCRIPTION: SEQ ID NO:45:

```
Val Phe Phe Ala Glu Asp Val Gly Ser Asn Lys Gly Ala Ile Ile Gly
 1               5                  10                  15

Leu Met Val Gly Gly Val Val Ile Ala Thr Val Ile Val Ile Thr Leu
             20                  25                  30

Val Met Leu Lys Lys Lys Gln Tyr Thr Ser Ile His His Gly Val Val Glu
         35                  40                  45
```